US006596280B1

(12) United States Patent
Vakharia et al.

(10) Patent No.: US 6,596,280 B1
(45) **Date of Patent: *Jul. 22, 2003**

(54) METHOD FOR GENERATING BIRNAVIRUS FROM SYNTHETIC RNA TRANSCRIPTS

(75) Inventors: Vikram N. Vakharia, Bowie, MD (US); Egbert Mundt, Millienhagen (DE)

(73) Assignee: University of Maryland Biotechnology Institute, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 09/147,771

(22) PCT Filed: Jul. 31, 1997

(86) PCT No.: PCT/US97/12955

§ 371 (c)(1),
(2), (4) Date: Apr. 30, 1999

(87) PCT Pub. No.: WO98/09646

PCT Pub. Date: Mar. 12, 1998

Related U.S. Application Data

(60) Continuation-in-part of application No. 09/198,913, filed on Nov. 24, 1998, now abandoned, which is a division of application No. 08/708,541, filed as application No. PCT/US97/12955 on Jul. 31, 1997.

(51) Int. Cl.[7] .......................... A61K 37/12; C12N 7/01; C12N 5/10; C12N 15/40; C12N 15/63

(52) U.S. Cl. ............................... 424/199.1; 424/204.1; 536/23.72; 435/320.1; 435/325; 435/235.1

(58) Field of Search ........................... 424/204.1, 199.1; 435/235.1, 320.1, 325, 252.3; 536/23.72

(56) References Cited

U.S. PATENT DOCUMENTS 5,871,744 A * 2/1999 Vakharia et al. ......... 424/205.1
6,274,147 B1 * 8/2001 Vakharia et al. ......... 424/199.1

OTHER PUBLICATIONS

Snyder et al. Avian Diseases 38:701–707, 1994.*

Mundt et al. Journal of Virology 71:5647–5651, 1997.*

Ganga et al, Journal of Virological Method 50:227–236, 1994.*

Roberts et al. Virology 247:1–6 (1998).*

Blake et al. Diseases of Aquatic Organisms 45(2): 89–102 (Abstract only cited).*

Elston. World Journal of Microbiology & Biotechnology 13(4): 393–403 (Abstract only cited).*

* cited by examiner

*Primary Examiner*—Mary E. Mosher
(74) *Attorney, Agent, or Firm*—Marianne Fuierer; Steven J. Hultquist; Yongzhi Yang

(57) ABSTRACT

A system for the generation of live Bimavirus such as infectious bursal disease virus (IBDV), a segmented double-stranded (ds) RNA virus of the Bimaviridae family, using synthetic transcripts derived from cloned DNA has been developed. Independent full-length cDNA clones were constructed which contained the entire coding and non-coding regions of RNA segments A and B of IBDV, respectively. Synthetic RNAs of both segments were produced by in vitro transcriptions of linearized plasmids with T7 RNA polymerase. Transfection of Vero cells with combined plus-sense transcripts of both segments generated infectious virus as early as 36 hours post-transfection. The development of a reverse genetics system for dsRNA viruses will greatly facilitate studies of the regulation of viral gene expression pathogenesis, and design of a new generation of live and inactivated vaccines.

15 Claims, 13 Drawing Sheets

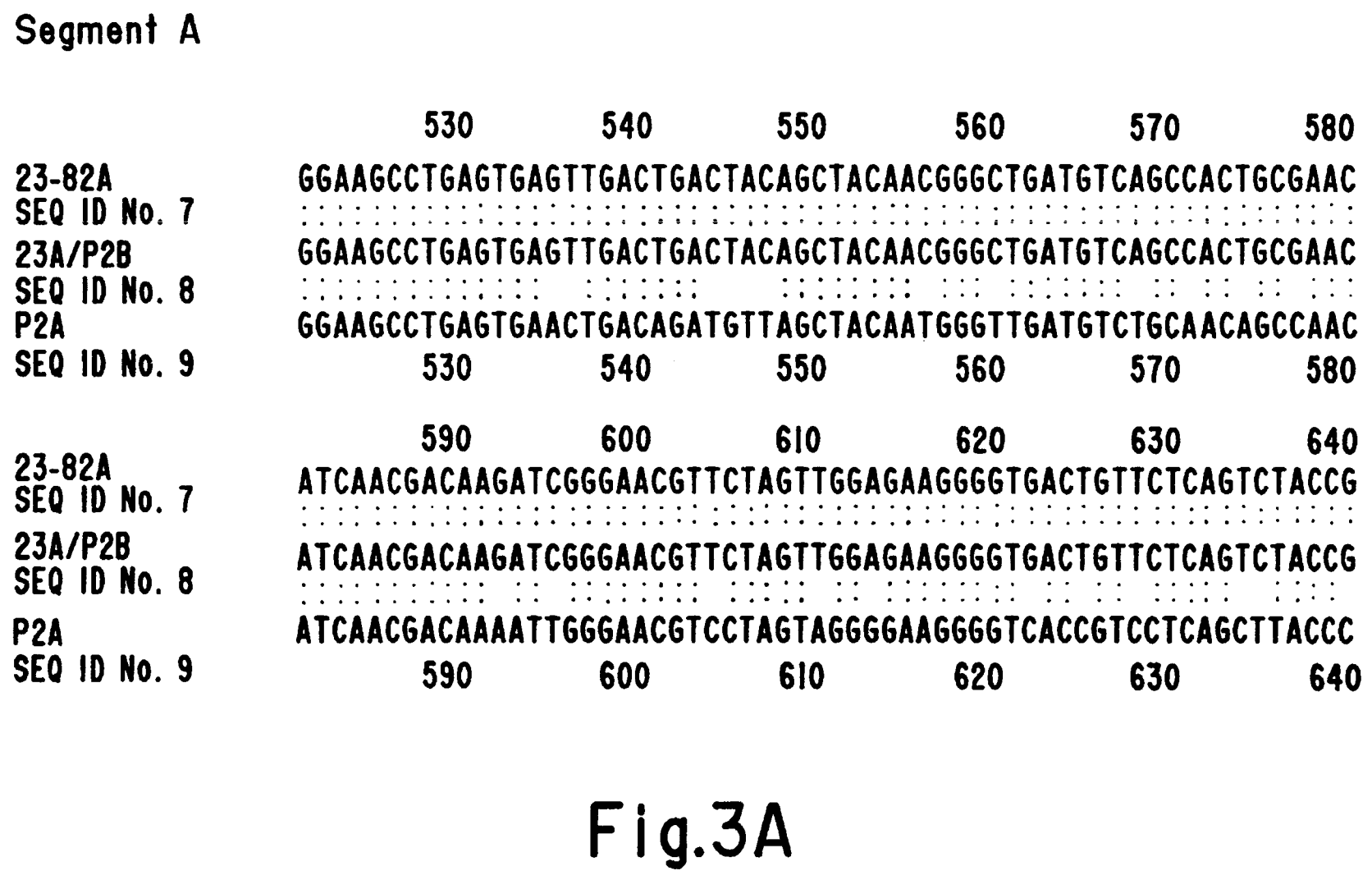

Segment A

```
                 530       540       550       560       570       580
23-82A           GGAAGCCTGAGTGAGTTGACTGACTACAGCTACAACGGGCTGATGTCAGCCACTGCGAAC
SEQ ID No. 7
23A/P2B          GGAAGCCTGAGTGAGTTGACTGACTACAGCTACAACGGGCTGATGTCAGCCACTGCGAAC
SEQ ID No. 8
P2A              GGAAGCCTGAGTGAACTGACAGATGTTAGCTACAATGGGTTGATGTCTGCAACAGCCAAC
SEQ ID No. 9     530       540       550       560       570       580

                 590       600       610       620       630       640
23-82A           ATCAACGACAAGATCGGGAACGTTCTAGTTGGAGAAGGGGTGACTGTTCTCAGTCTACCG
SEQ ID No. 7
23A/P2B          ATCAACGACAAGATCGGGAACGTTCTAGTTGGAGAAGGGGTGACTGTTCTCAGTCTACCG
SEQ ID No. 8
P2A              ATCAACGACAAAATTGGGAACGTCCTAGTAGGGGAAGGGGTCACCGTCCTCAGCTTACCC
SEQ ID No. 9     590       600       610       620       630       640
```

Fig.3A

Figure 3B:
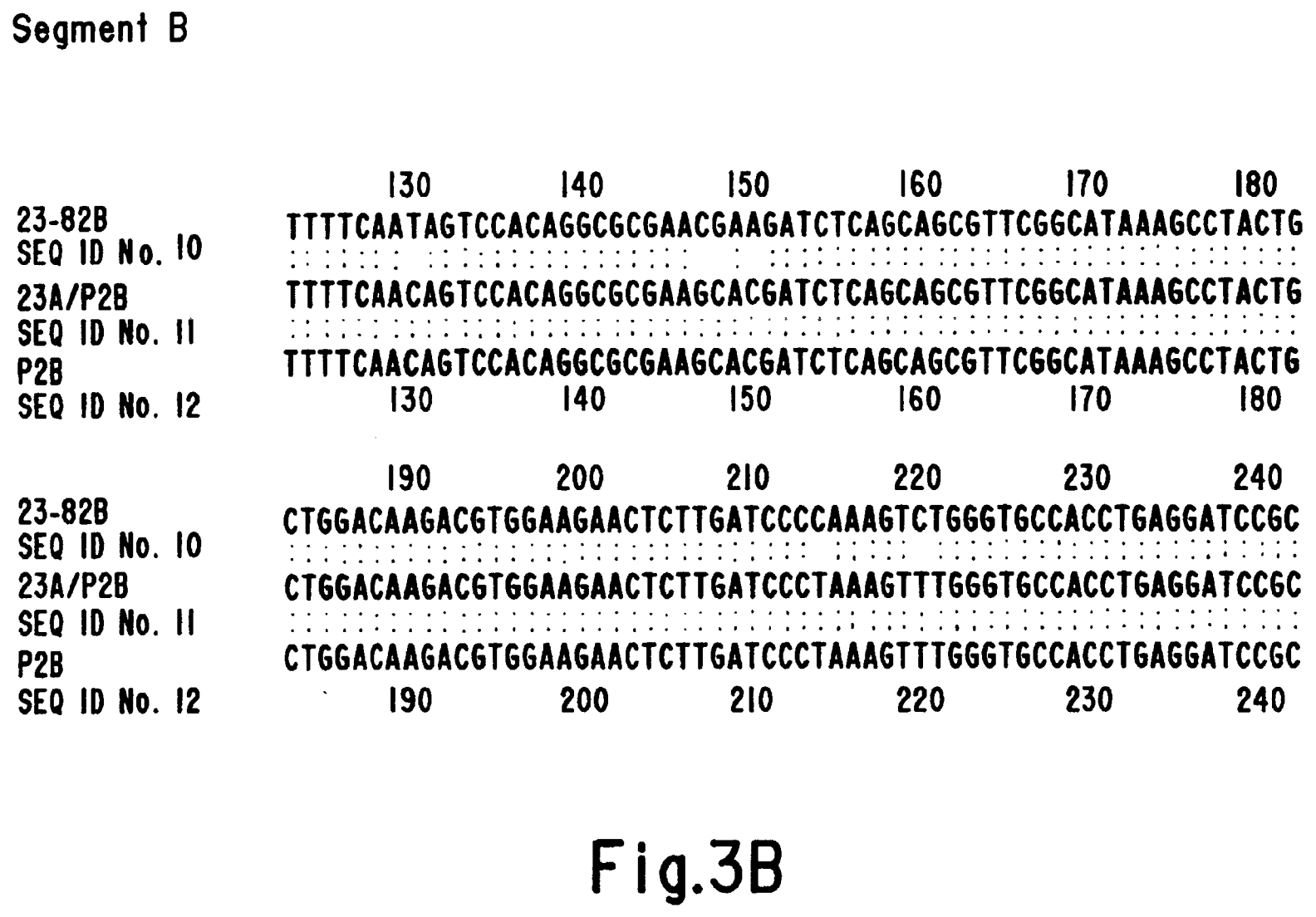

Segment B

```
                                130        140        150        160        170        180
23-82B               TTTTCAATAGTCCACAGGCGCGAACGAAGATCTCAGCAGCGTTCGGCATAAAGCCTACTG
SEQ ID No. 10
23A/P2B              TTTTCAACAGTCCACAGGCGCGAAGCACGATCTCAGCAGCGTTCGGCATAAAGCCTACTG
SEQ ID No. 11
P2B                  TTTTCAACAGTCCACAGGCGCGAAGCACGATCTCAGCAGCGTTCGGCATAAAGCCTACTG
SEQ ID No. 12                   130        140        150        160        170        180

                                190        200        210        220        230        240
23-82B               CTGGACAAGACGTGGAAGAACTCTTGATCCCCAAAGTCTGGGTGCCACCTGAGGATCCGC
SEQ ID No. 10
23A/P2B              CTGGACAAGACGTGGAAGAACTCTTGATCCCTAAAGTTTGGGTGCCACCTGAGGATCCGC
SEQ ID No. 11
P2B                  CTGGACAAGACGTGGAAGAACTCTTGATCCCTAAAGTTTGGGTGCCACCTGAGGATCCGC
SEQ ID No. 12                   190        200        210        220        230        240
```

```
        10        20        30        40        50        60        70
         |         |         |         |         |         |         |
   1 GGATACGATCGGTCTGACCCCGGGGGAGTCACCCGGGGACAGGCCATCACTGCCTTGTTCCTGGTTGGAA
  71 CTCCTCTTTCTGCTGTACTATCGTTGATGGTGAGTAGAGATCAGACAAACGATCGCAGCGATGACAAACC
 141 TGATGGATCACACCCAACAGATTGTTCCGTTCATACGGAGCCTTCTGATGCCAACGACCGGACCGGCGTC
 211 CATTCCGGACGACACCCTGGAGAAGCACACACTCAGGTCCGAAACCTCGACTTACAACTTGACTGTAGGG
 281 GATACAGGGTCAGGACTAATTGTCTTTTTCCCTGGATTCCCTGGTTCAGTTGTAGGTGCTCACTACACAC
 351 TGCAGAGCAGTGGGAACTACCAATTCGACCAGATGCTCCTGACAGCGCAGAACCTGCCTGCCAGCTACAA
 421 CTACTGCAGGCTAGTGAGCAGGAGTCTAACCGTACGGTCAAGCACACTCCCTGGTGGCGTTTATGCACTA
 491 AACGGAACCATAAACGCAGTGACCTTCCACGGAAGCCTGAGTGAGTTGACTGACTACAGCTACAACGGGC
 561 TGATGTCAGCCACTGCGAACATCAACGACAAGATCGGGAACGTTCTAGTTGGAGAAGGGGTGACTGTTCT
 631 CAGTCTACCGACTTCATATGACCTTAGTTATGTGAGACTCGGTGACCCCATCCCCGCAGCAGGACTCGAC
 701 CCGAAGTTGATGGCCACGTGCGACAGTAGTGACAGACCCAGAGTCTACACCATAACAGCTGCAGATGAAT
 771 ACCAATTCTCGTCACAACTCATCCCGAGTGGCGTGAAGACCACACTGTTCTCCGCCAACATCGATGCTCT
 841 CACCAGCTTCAGCGTTGGTGGTGAGCTTGTCTTCAGCCAAGTAACGATCCAAAGCATTGAAGTGGACGTC
 911 ACCATTCACTTCATTGGGTTTGACGGGACAGACGTAGCAGTCAAGGCAGTTGCAACAGACTTTGGGCTGA
 981 CAACTGGGACAAACAACCTTGTGCCATTCAACCTGGTGGTCCCAACAAATGAGATCACCCAGCCCATCAC
1051 TTCCATGAAACTAGAGGTTGTGACCTACAAGATTGGCGGCACCGCTGGTGACCCAATATCATGGACAGTG
1121 AGTGGTACACTAGCTGTGACGGTGCACGGAGGCAACTACCCTGGGGCTCTCCGTCCTGTCACCCTGGTGG
1191 CCTATGAACGAGTGGCTGCAGGATCTGTTGTCACAGTTGCAGGGGTGAGCAACTTCGAGCTAATCCCCAA
1261 CCCTGAGCTTGCAAAGAACCTAGTTACAGAGTATGGCCGCTTTGACCCCGGAGCAATGAACTACACCAAA
1331 CTAATACTGAGTGAGAGAGATCGTCTAGGCATCAAGACAGTCTGGCCCACCAGGGAGTACACCGATTTGA
1401 GGGAGTACTTCATGGAGGTTGCAGATCTCAACTCACCCCTAAAGATTGCAGGAGCATTTGGCTTTAAGGA
1471 CATAATCCGAGCCATTCGGAAGATTGCGGTGCCAGTGGTATCCACACTCTTCCCTCCAGCTGCACCCCTA
1541 GCACATGCAATCGGAGAAGGTGTAGACTACCTCCTGGGCGACGAGGCCCAAGCAGCCTCAGGGACAGCTC
1611 GAGCCGCGTCAGGAAAAGCTAGAGCTGCCTCAGGACGAATAAGGCAGCTAACTCTCGCAGCTGACAAGGG
1681 GTGCGAGGTAGTCGCCAACATGTTCCAGGTGCCCCAGAATCCCATTGTTGATGGCATTCTGGCATCCCCA
1751 GGAATCCTGCGTGGCGCACACAACCTCGACTGCGTGCTATGGGAGGGAGCCACTCTTTTCCCTGTTGTCA
```

1821 TTACGACACTCGAGGATGAGCTGACCCCCAAGGCACTGAACAGCAAAATGTTTGCTGTCATTGAAGGTGT
1891 GCGAGAGGACCTCCAGCCTCCATCCCAACGGGGATCCTTCATTCGAACTCTCTCTGGCCATAGAGTCTAT
1961 GGCTATGCCCCAGACGGAGTACTGCCTCTGGAGACCGGGAGAGACTACACCGTTGTCCCAATTGATGATG
2031 TGTGGGACGATAGCATAATGCTGTCGCAGGACCCCATACCTCCAATCATAGGGAACAGCGGCAACCTAGC
2101 CATAGCATACATGGATGTCTTCAGGCCCAAGGTCCCCATCCACGTGGCTATGACAGGGGCCCTCAATGCC
2171 CGCGGTGAGATCGAGAGTGTTACGTTCCGVAGCACCAAACTCGCCACAGCCCACCGACTTGGCATGAAGT
2241 TAGCTGGTCCTGGAGCCTATGACATTAATACAGGACCTAACTGGGCAACGTTCGTCAAACGTTTCCCTCA
2311 CAATCCCCGAGACTGGGACAGGTTGCCCTACCTCAACCTTCCTTATCTCCCACCAACAGCAGGACGTCAG
2381 TTCCATCTAGCCCTGGCTGCCTCCGAGTTCAAAGAGACCCCAGAACTCGAAGACGCTGTGCGCGCAATGG
2451 ATGCCGCTGCAAATGCCGACCCATTGTTCCGCTCAGCTCTCCAGGTCTTCATGTGGTTGGAAGAAAACGG
2521 GATTGTGACCGACATGGCTAACTTCGCCCTCAGCGACCCAAACGCGCATAGGATGAAAAACTTCCTAGCA
2591 AACGCACCCCAGGCTGGAAGCAAGTCGCAGAGGGCCAAGTATGGCACGGCAGGCTACGGAGTGGAGGCTC
2661 GAGGCCCCACACCAGAAGAGGCACAGAGGGAAAAAGACACACGGATCTCCAAGAAGATGGAAACAATGGG
2731 CATCTACTTCGCGACACCGGAATGGGTGGCTCTCAACGGGCACCGAGGCCCAAGCCCCGGCCAACTCAAG
2801 TACTGGCAAAACACAAGAGAAATACCAGAGCCCAATGAGGACTACCCAGACTATGTGCACGCGGAGAAGA
2871 GCCGGTTGGCGTCAGAAGAACAGATCCTACGGGCAGCCACGTCGATCTACGGGGCTCCAGGACAGGCTGA
2941 ACCACCCCAGGCCTTCATAGACGAGGTCGCCAGGGTCTATGAAATCAACCATGGGCGTGGTCCAAACCAG
3011 GAGCAGATGAAGGACCTGCTCCTGACTGCGATGGAGATGAAGCATCGCAATCCCAGGCGGGCTCCACCAA
3081 AGCCAAAGCCAAAACCCAATGCTCCATCACAGAGACCCCCTGGACGGCTGGGCCGCTGGATCAGGACGGT
3151 CTCCGACGAGGACTTGGAGTGAGGCTCCTGGGAGTCTCCCGACACTACCCGCGCAGGTGTGGACACCAAT
3221 TCGGCCTTCTACCATCCCAAATTGGATCCGTTCGCGGGTCCCCT

Total number of bases is: 3264.
DNA sequence composition: 834 A; 942 C; 853 G; 635 T;

Sequence name: 23-82A (SEQ ID NOS: 31 and 33)

```
         10        20        30        40        50        60        70
          |         |         |         |         |         |         |
   1 GGATACGATCGGTCTGACCCCGGGGGAGTCACCCGGGGACAGGCCGTCAAGGCCTTGTTCCAGGATGGGA
  71 CTCCTCCTTCTACAACGCTATCATTGATGGTTAGTAGAGATCAGACAAACGATCGCAGCGATGACAAACC
 141 TGCAAGATCAAACCCAACAGATTGTTCCGTTCATACGGAGCCTTCTGATGCCAACAACCGGACCGGCGTC
 211 CATTCCGGACGACACCCTGGAGAAGCACACTCTCAGGTCAGAGACCTCGACCTACAATTTGACTGTGGGG
 281 GACACAGGGTCAGGGCTAATTGTCTTTTTCCCTGGATTCCCTGGCTCAATTGTGGGTGCTCACTACACAC
 351 TGCAGGGCAATGGGAACTACAAGTTCGATCAGATGCTCCTGACTGCCCAGAACCTACCGGCCAGTTACAA
 421 CTACTGCAGGCTAGTGAGTCGGAGTCTCACAGTGAGGTCAAGCACACTTCCTGGTGGCGTTTATGCACTA
 491 AACGGCACCATAAACGCCGTGACCTTCCAAGGAAGCCTGAGTGAACTGACAGATGTTAGCTACAATGGGT
 561 TGATGTCTGCAACAGCCAACATCAACGACAAAATTGGGAACGTCCTAGTAGGGGAAGGGGTCACCGTCCT
 631 CAGCTTACCCACATCATATGATCTTGGGTATGTGAGGCTTGGTGACCCCATTCCCGCAATAGGGCTTGAC
 701 CCAAAAATGGTAGCCACATGTGACAGCAGTGACAGGCCCAGAGTCTACACCATAACTGCAGCCGATGATT
 771 ACCAATTCTCATCACAGTACCAACCAGGTGGGGTAACAATCACACTGTTCTCAGCCAACATTGATGCCAT
 841 CACAAGCCTCAGCGTTGGGGGAGAGCTCGTGTTTCAAACAAGCGTCCACGGCCTTGTACTGGGCGCCACC
 911 ATCTACCTCATAGGCTTTGATGGGACAACGGTAATCACCAGGGCTGTGGCCGCAAACAATGGGCTGACGA
 981 CCGGCACCGACAACCTTATGCCATTCAATCTTGTGATTCCAACAAACGAGATAACCCAGCCAATCACATC
1051 CATCAAACTGGAGATAGTGACCTCCAAAAGTGGTGGTCAGGCAGGGGATCAGATGTCATGGTCGGCAAGA
1121 GGGAGCCTAGCAGTGACGATCCATGGTGGCAACTATCCAGGGGCCCTCCGTCCCGTCACGCTAGTGGCCT
1191 ACGAAAGAGTGGCAACAGGATCCGTCGTTACGGTCGCTGGGGTGAGCAACTTCGAGCTGATCCCAAATCC
1261 TGAACTAGCAAAGAACCTGGTTACAGAATACGGCCGATTTGACCCAGGAGCCATGAACTACACAAAATTG
1331 ATACTGAGTGAGAGGGACCGTCTTGGCATCAAGACCGTCTGGCCAACAAGGGAGTACACTGACTTTCGTG
1401 AATACTTCATGGAGGTGGCCGACCTCAACTCTCCCCTGAAGATTGCAGGAGCATTCGGCTTCAAAGACAT
1471 AATCCGGGCCATAAGGAGGATAGCTGTGCCGGTGGTCTCCACATTGTTCCCACCTGCCGCTCCCCTAGCC
1541 CATGCAATTGGGGAAGGTGTAGACTACCTGCTGGGCGATGAGGCACAGGCTGCTTCAGGAACTGCTCGAG
1611 CCGCGTCAGGAAAAGCAAGAGCTGCCTCAGGCCGCATAAGGCAGCTGACTCTCGCCGCCGACAAGGGGTA
1681 CGAGGTAGTCGCGAATCTATTCCAGGTGCCCCAGAATCCCGTAGTCGACGGGATTCTTGCTTCACCTGGG
1751 GTACTCCGCGGTGCACACAACCTCGACTGCGTGTTAAGAGAGGGTGCCACGCTATTCCCTGTGGTTATTA
```

```
1821 CGACAGTGGAAGACGCCATGACACCCAAAGCATTGAACAGCAAAATGTTTGCTGTCATTGAAGGCGTGCG
1891 AGAAGACCTCCAACCTCCATCTCAAAGAGGATCCTTCATACGAACTCTCTCTGGACACAGAGTCTATGGA
1961 TATGCTCCAGATGGGGTACTTCCACTGGAGACTGGGAGAGACTACACCGTTGTCCCAATAGATGATGTCT
2031 GGGACGACAGCATTATGCTGTCCAAAGATCCCATACCTCCTATTGTGGGAAACAGTGGAAATCTAGCCAT
2101 AGCTTACATGGATGTGTTTCGACCCAAAGTCCCAATCCATGTGGCTATGACGGGAGCCCTCAATGCTTGT
2171 GGCGAGATTGAGAAAGTAAGCTTTAGAAGCACCAAGCTCGCCACTGCACACCGACTTGGCCTTAGGTTGG
2241 CTGGTCCCGGAGCATTCGATGTAAACACCGGGCCCAACTGGGCAACGTTCATCAAACGTTTCCCTCACAA
2311 TCCACGCCACTGGGACAGGCTCCCCTACCTCAACCTACCATACCTTCCACCCAATGCAGGACGCCAGTAC
2381 CACCTTGCCATGGCTGCATCAGAGTTCAAAGAGACCCCCGAACTCGAGAGTGCCGTCAGAGCAATGGAAG
2451 CAGCAGCCAACGTGGACCCACTATTCCAATCTGCACTCAGTGTGTTCATGTGGCTGGAAGAGAATGGGAT
2521 TGTGACTGACATGGCCAACTTCGCACTCAGCGACCCGAACGCCCATCGGATGCGAAATTTTCTTGCAAAC
2591 GCACCACAAGCAGGCAGCAAGTCGCAAAGGGCCAAGTACGGGACAGCAGGCTACGGAGTGGAGGCTCGGG
2661 GCCCCACACCAGAGGAAGCACAGAGGGAAAAAGACACACGGATCTCAAAGAAGATGGAGACCATGGGCAT
2731 CTACTTTGCAACACCAGAATGGGTAGCACTCAATGGGCACCGAGGGCCAAGCCCCGGCCAGCTAAAGTAC
2801 TGGCAGAACACACGAGAAATACCGGACCCAAACGAGGACTATCTAGACTACGTGCATGCAGAGAAGAGCC
2871 GGTTGGCATCAGAAGAACAAATCCTAAGGGCAGCTACGTCGATCTACGGGGCTCCAGGACAGGCAGAGCC
2941 ACCCCAAGCTTTCATAGACGAAGTTGCCAAAGTCTATGAAATCAACCATGGACGTGGCCCAAACCAAGAA
3011 CAGATGAAAGATCTGCTCTTGACTGCGATGGAGATGAAGCATCGCAATCCCAGGCGGGCTCTACCAAAGC
3081 CCAAGCCAAAACCCAATGCTCCAACACAGAGACCCCCTGGTCGGCTGGGCCGCTGGATCAGGACCGTCTC
3151 TGATGAGGACCTTGAGTGAGGCTCCTGGGAGTCTCCCGACACCACCCGCGCAGGTGTGGACACCAATTCG
3221 GCCTTACAACATCCCAAATTGGATCCGTTCGCGGGTCCCCT
```

Total number of bases Is: 3261.

DNA sequence composition: 873 A; 909 C; 847 G; 632 T; 0 OTHER;

Sequence name: D78F (SEQ ID NOS: 27 and 29)

```
           10        20        30        40        50        60        70
            |         |         |         |         |         |         |
   1 GGATACGATGGGTCTGACCCTCTGGGAGTCACGAATTAACGTGGCTACTAGGGGCGATACCCGCCGCTGG
  71 CCGCCACGTTAGTGGCTCCTCTTCTTGATGATTCTGCCACCATGAGTGACATTTTCAACAGTCCACAGGC
 141 GCGAAGCACGATCTCAGCAGCGTTCGGCATAAAGCCTACTGCTGGACAAGACGTGGAAGAACTCTTGATC
 211 CCTAAAGTTTGGGTGCCACCTGAGGATCCGCTTGCCAGCCCTAGTCGACTGGCAAAGTTCCTCAGAGAGA
 281 ACGGCTACAAAGTTTTGCAGCCACGGTCTCTGCCCGAGAATGAGGAGTATGAGACCGACCAAATACTCCC
 351 AGACTTAGCATGGATGCGACAGATAGAAGGGGCTGTTTTAAAACCCACTCTATCTCTCCCTATTGGAGAT
 421 CAGGAGTACTTCCCAAAGTACTACCCAACACATCGCCCTAGCAAGGAGAAGCCCAATGCGTACCCGCCAG
 491 ACATCGCACTACTCAAGCAGATGATTTACCTGTTTCTCCAGGTTCCAGAGGCCAACGAGGGCCTAAAGGA
 561 TGAAGTAACCCTCTTGACCCAAAACATAAGGGACAAGGCCTATGGAAGTGGGACCTACATGGGACAAGCA
 631 AATCGACTTGTGGCCATGAAGGAGGTCGCCACTGGAAGAAACCCAAACAAGGATCCTCTAAAGCTTGGGT
 701 ACACTTTTGAGAGCATCGCGCAGCTACTTGACATCACACTACCGGTAGGCCCACCCGGTGAGGATGACAA
 771 GCCCTGGGTGCCACTCACAAGAGTGCCGTCACGGATGTTGGTGCTGACGGGAGACGTAGATGGCGACTTT
 841 GAGGTTGAAGATTACCTTCCCAAAATCAACCTCAAGTCATCAAGTGGACTACCATATGTAGGTCGCACCA
 911 AAGGAGAGACAATTGGCGAGATGATAGCTATCTCAAACCAGTTTCTCAGAGAGCTATCAACACTGTTGAA
 981 GCAAGGTGCAGGGACAAAGGGGTCAAACAAGAAGAAGCTACTCAGCATGTTAAGTGACTATTGGTACTTA
1051 TCATGCGGGCTTTTGTTTCCAAAGGCTGAAAGGTACGACAAAAGTACATGGCTCACCAAGACCCGGAACA
1121 TATGGTCAGCTCCATCCCCAACACACCTCATGATCTCTATGATCACCTGGCCCGTGATGTCCAACAGCCC
1191 AAATAACGTGTTGAACATTGAAGGGTGTCCATCACTCTACAAATTCAACCCGTTCAGAGGAGGGTTGAAC
1261 AGGATCGTCGAGTGGATATTGGCCCCGGAAGAACCCAAGGCTCTTGTATATGCGGACAACATATACATTG
1331 TCCACTCAAACACGTGGTACTCAATTGACCTAGAGAAGGGTGAGGCAAACTGCACTCGCCAACACATGCA
1401 AGCCGCAATGTACTACATACTCACCAGAGGGTGGTCAGACAACGGCGACCCAATGTTCAATCAAACATGG
1471 GCCACCTTTGCCATGAACATTGCCCCTGCTCTAGTGGTGGACTCATCGTGCCTGATAATGAACCTGCAAA
1541 TTAAGACCTATGGTCAAGGCAGCGGGAATGCAGCCACGTTCATCAACAACCACCTCTTGAGCACACTAGT
1611 GCTTGACCAGTGGAACCTGATGAGACAGCCCAGACCAGACAGCGAGGAGTTCAAATCAATTGAGGACAAG
1681 CTAGGTATCAACTTTAAGATTGAGAGGTCCATTGATGATATCAGGGGCAAGCTGAGACAGCTTGTCCTCC
1751 TTGCACAACCAGGGTACCTGAGTGGGGGGGTTGAACCAGAACAATCCAGCCCAACTGTTGAGCTTGACCT
```

1821 ACTAGGGTGGTCAGCTACATACAGCAAAGATCTCGGGATCTATGTGCCGGTGCTTGACAAGGAACGCCTA
1891 TTTTGTTCTGCTGCGTATCCCAAGGGAGTAGAGAACAAGAGTCTCAAGTCCAAAGTCGGGATCGAGCAGG
1961 CATACAAGGTAGTCAGGTATGAGGCGTTGAGGTTGGTAGGTGGTTGGAACTACCCACTCCTGAACAAAGC
2031 CTGCAAGAATAACGCAGGCGCCGCTCGGCGGCATCTGGAGGCCAAGGGGTTCCCACTCGACGAGTTCCTA
2101 GCCGAGTGGTCTGAGCTGTCAGAGTTCGGTGAGGCCTTCGAAGGCTTCAATATCAAGCTGACCGTAACAT
2171 CTGAGAGCCTAGCCGAACTGAACAAGCCAGTACCCCCCAAGCCCCCAAATGTCAACAGACCAGTCAACAC
2241 TGGGGGACTCAAGGCAGTCAGCAACGCCCTCAAGACCGGTCGGTACAGGAACGAAGCCGGACTGAGTGGT
2311 CTCGTCCTTCTAGCCACAGCAAGAAGCCGTCTGCAAGATGCAGTTAAGGCCAAGGCAGAAGCCGAGAAAC
2381 TCCACAAGTCCAAGCCAGACGACCCCGATGCAGACTGGTTCGAAAGATCAGAAACTCTGTCAGACCTTCT
2451 GGAGAAAGCCGACATCGCCAGCAAGGTCGCCCACTCAGCACTCGTGGAAACAAGCGACGCCCTTGAAGCA
2521 GTTCAGTCGACTTCCGTGTACACCCCCAAGTACCCAGAAGTCAAGAACCCACAGACCGCCTCCAACCCCG
2591 TTGTTGGGCTCCACCTGCCCGCCAAGAGAGCCACCGGTGTCCAGGCCGCTCTTCTCGGAGCAGGAACGAG
2661 CAGACCAATGGGGATGGAGGCCCCAACACGGTCCAAGAACGCCGTGAAAATGGCCAAACGGCGGCAACGC
2731 CAAAAGGAGAGCCGCTAACAGCCATGATGGGAACCACTCAAGAAGAGGACACTAATCCCAGACCCCGTAT
2801 CCCCGGCCTTCGCCTGCGGGGGCCCCC

Total number of bases is: 2827.

DNA sequence composition: 796 A; 770 C; 724 G; 537 T; 0 OTHER;

Sequence name: P2B (SEQ ID No: 25)

Fig.6B

METHOD FOR GENERATING BIRNAVIRUS FROM SYNTHETIC RNA TRANSCRIPTS

CROSS-REFERENCE TO RELATED APPLICATIONS

This application is a continuation-in-part of application Ser. No. 09/198,913, filed on Nov. 14, 1998, now abandoned, which is a divisional of Ser. No. 08/708,541, filed on Sep. 5, 1996, now U.S. Pat. No. 5,871,744. The present application is a national stage entry of PCT/US97/12955 filed on Jul. 31, 1997.

BACKGROUND OF THE INVENTION

Infectious bursal disease virus (IBDV), a member of the Bimaviridae family, is the causative agent of a highly immunosuppressive disease in young chickens (Kibenge, F. S. B., et al., *J. Gen. Virol*., 69, 1757–1775 (1988)). Infectious bursal disease (IBD) or Gumboro disease is characterized by the destruction of lymphoid follicles in the bursa of Fabricius. In a fully susceptible chicken flock of 3–6 weeks of age the clinical disease causes severe immunosuppression, and is responsible for losses due to impaired growth, decreased feed efficiency, and death. Susceptible chickens less than 3 weeks old do not exhibit outward clinical signs of the disease but have a marked infection characterized by gross lesions of the bursa.

The virus associated with the symptoms of the disease is called infectious bursal disease virus (IBDV). IBDV is a pathogen of major economic importance to the nation and world's poultry industries. It causes severe immunodeficiency in young chickens by destruction of precursors of antibody-production B cells in the bursa of Fabricius. Immunosuppression causes increased susceptibility to other diseases, and interferes with effective vaccination against Newcastle disease, Marek's disease and infectious bronchitis disease viruses.

There are two known serotypes of IBDV. Serotype I viruses are pathogenic to chickens whereas serotype II viruses infect chickens and turkeys. The infection of turkeys is presently of unknown clinical significance.

IBDV belongs to a group of viruses called Bimaviridae which includes other bisegmented RNA viruses such as infectious pancreatic necrosis virus (fish), tellina virus and oyster virus (bivalve mollusks) and drosophila X virus (fruit fly). These viruses all contain high molecular weight (MW) double-stranded RNA genomes.

The capsid of the IBDV virion consists of several structural proteins. As many as nine structural proteins have been reported but there is evidence that some of these may have a precursor-product relationship (Kibenge, F. S. B., et al., *J. Gen. Virol*., 69, 1757–1775 (1988)). The designation and molecular weights of the viral proteins (VP) are as shown below.

| Viral Protein | Molecular Weight |
|---|---|
| VP1 | 90 kDa |
| VP2 | 41 kDa |
| VP3 | 32 kDa |
| VP4 | 25 kDa |
| VP5 | 17 kDa |

Two segments of double-stranded RNA were identified in the genome of IBDV. The IBDV genome consists of two segments of double-stranded (ds)RNA that vary between 2827 (segment B) to 3261 (segment A) nucleotide base pairs (Mundt, E. et al., *Virology*, 209, 10–18 (1995)). The larger segment A encodes a polyprotein which is cleaved by autoproteolysis to form mature viral proteins VP2, VP3 and VP4 (Hudson, P. J. et al., *Nucleic Acids Res*., 14, 5001–5012 (1986)). VP2 and VP3 are the major structural proteins of the virion. VP2 is the major host-protective immunogen of IBDV, and contains the antigenic regions responsible for the induction of neutralizing antibodies (Azad, et al., *Virology*, 161, 145–152 (1987)). A second open reading frame (ORF), preceding and partially overlapping the polyprotein gene, encodes a, protein (VP5) of unknown function that is present in IBDV-infected cells (Mundt, E., et al., *J Gen. Virol*., 76, 437–443, (1995)). The smaller segment B encodes VP1, a 90-kDa multifunctional protein with polymerase and capping enzyme activities (Spies, U., et al., *Virus Res*., 8, 127–140 (1987); Spies, U., et al., *J. Gen. Virol*., 71, 977–981 (1990)).

It has been demonstrated that the VP2 protein is the major host protective immunogen of IBDV, and that it contains the antigenic region responsible for the induction of neutralizing antibodies. The region containing the neutralization site has been shown to be highly conformation-dependent. The VP3 protein has been considered to be a group-specific antigen because it is recognized by monoclonal antibodies directed against it from strains of both serotype I and II viruses. The VP4 protein appears to be a virus-coded protease that is involved in the processing of a precursor polyprotein of the VP2, VP3 and VP4 proteins.

Although the nucleotide sequences for genome segments A and B of various IBDV strains have been published, it was only recently that the complete 5'- and 3'-noncoding sequences of both segments were determined. The 5'-noncoding region of IBDV segments A and B contain a consensus sequence of 32 nucleotides, whereas the 3'-noncoding terminal sequences of both segments are unrelated, but conserved among IBDV strains of the same serotype (Mundt, E. et al., *Virology*, 209, 10–18 (1995)). These terminii might contain sequences important in packaging and in the regulation of IBDV gene expression, as demonstrated for other dsRNA containing viruses such as mammalian and plant reoviruses, and rotaviruses (Anzola, et al., *Proc. Natl. Acad. Sci. USA*, 84, 8301–8305 (1987); Zou, S., et al., *Virology*, 186, 377–388 (1992); Gorziglia, M. I., et al., *Proc. Natl. Acad. Sci. USA*, 89, 5784–5788 (1992)).

In recent years, a number of infectious animal RNA viruses have been generated from cloned cDNA using transcripts produced by DNA-dependent RNA polymerase (Boyer, J. C., et al., *Virology*, 198, 415–426 (1994)). For example poliovirus, a plus-stranded RNA virus; influenza virus, a segmented negative-stranded RNA virus; rabies virus, a non-segmented negative-stranded RNA virus; all were recovered from cloned cDNAs of their respective genomes (van der Werf, S., et al., *Proc. Natl. Acad. Sci. USA*, 83, 2330–2334 (1986); Enami, M., et al., *Proc. Natl. Acad. Sci. USA*, 87, 3802–3805 (1990); Schnell, M. J., et al., *EMBO J*., 13, 41954205 (1994)). For reovirus, it was shown that transfection of cells with a combination of SSRNA, dsRNA and in vitro translated reovirus products generated infectious reovirus when complemented with a helper virus from a different serotype (Roner, M. R., et al., *Virology*, 179, 845–852 (1990)). However, to date, there has been no report of a recovered infectious virus of segmented dsRNA genome from synthetic RNAs only.

SUMMARY OF THE INVENTION

This invention relates to the infectious bursal disease virus (IBDV) that is associated with Gumboro disease of young chickens. More particularly, this invention relates to a system for the generation of infectious bursal disease virus (IBDV) using synthetic transcripts derived from cloned cDNA. The present invention will facilitate studies of the regulation of viral gene expression, pathogenesis and design of a new generation of live and inactivated vaccines.

DETAILED DESCRIPTION OF THE INVENTION

In an effort to develop a reverse genetics system for IBDV, three independent full-length cDNA clones which contain segment A of serotype I strain D78 or serotype II strain 23/82 and segment B of the serotype I strain P2, respectively, were constructed. Synthetic RNAs of segments A and B were produced by in vitro transcription reaction on linearized plasmids with T7 RNA polymerase. Transcripts of these segments, either untreated or treated with DNase or RNase, were evaluated for the generation of infectious virus by transfection of Vero cells.

The present inventors have demonstrated that synthetic transcripts derived from cloned DNA corresponding to the entire genome of a segmented dsRNA animal virus can give rise to a replicating virus. The recovery of infectious virus after transfecting cells with synthetic plus-sense RNAs derived from cloned cDNA of a virus with a dsRNA genome (IBDV) completes the quest of generating reverse infectious systems for RNA viruses. A number of investigators have generated infectious animal RNA viruses from cloned cDNA (Boyer, J. C., et al., *Virology*, 198, 415–426 (1994)). Van der Werf et al. were first to generate poliovirus, a plus-stranded RNA virus, using synthetic RNA produced by T7 RNA polymerase on cloned cDNA template (van der Werf, S., et al., *Proc. Natl. Acad. Sci. USA*, 83, 2330–2334 (1986)). later, Enami et al. rescued influenza virus, a segmented negative-stranded RNA virus (Enami, M., et al., *Proc. Natl. Acad. Sci. USA*, 87, 3802–3805 (1990)); and Schnell et al. generated rabies virus, a non-segmented negative-stranded RNA virus, from cloned cDNAs of their respective genomes (Schnell, M. J., et al., *EMBO J.*, 13, 4195–4205 (1994)). Roner et al. developed an infectious system for a segmented dsRNA reovirus by transfecting cells with a combination of synthetic ssRNA, dsRNA, in vitro translated reovirus products, and complemented with a helper virus of different serotype (Roner, M. R., et al., *Virology*, 179, 845–852 (1990)). The resulting virus was discriminated from the helper virus by plaque assay. However, in this system the use of a helper virus was necessary. In contrast, the presently described reverse genetics system of IBDV does not require a helper virus or other viral proteins. Transfection of cells with plus-sense RNAs of both segments was sufficient to generate infectious virus (IBDV). The fate of the additional one or four nucleotides, respectively, transcribed at the 3'-end of segment A was not determined. However, this did not prevent the replication of the viral dsRNA. Similar effects were observed for plus-stranded RNA viruses by different investigators (Boyer, J. C., et al., *Virology*, 198, 415–426 (1994)).

Transfection of plus-sense RNAs of both segments into the same cell was necessary for the successful recovery of IBDV. Transfected RNAs of both segments had to be translated by the cellular translation machinery. The polyprotein of segment A was presumably processed into VP2, VP3 and VP4 proteins which form the viral capsid. The translated protein VP1 of segment B probably acted as a RNA-dependent RNA polymerase and transcribed minus-strands from synthetic plus-strands of both segments, and the reaction products formed dsRNA. Recently, Dobos reported that in vitro transcription by the virion RNA-dependent RNA polymerase of infectious pancreatic necrosis virus (IPNV), a prototype virus of the Bimaviridae family, is primed by VP1 and then proceeds via an asymmetric, semiconservative, strand-displacement mechanism to synthesize only plus strands during replication of the viral genome (Dobos, P., *Virology*, 208, 10–25 (1995)). The present system shows that synthesis of minus-strands proceeds on the plus-strands. Whether the resulting transcribed minus-strand RNA serves as a template for the transcription of plus-strands or not remains the subject of further investigation.

To prove that the infectious IBDV contained in the supernatants of transfected cells was indeed derived from the synthetic transcripts, an artificial chimera was generated containing segment A of a serotype II strain and segment B of a serotype I strain. Sequence analysis verified this genome combination. The results also indicate that the terminal sequence motifs described by Mundt and Müller are probably responsible for replication, sorting and packaging of the viral genome (Mundt, E. et al., *Virology*, 209, 10–18 (1995)). Presence of serotype-specific terminal sequences obviously does not prevent proper replication of serotype II A segment by the action of the RNA-dependent RNA polymerase VP1 of the serotype I segment B. The ability to create recombinant viruses will greatly help in analyzing the precise function of serotype-specific and serotype-common terminal sequences.

The recovery of infectious IBDV demonstrates that only the plus-strand RNAs of both segments are sufficient to initiate replication of dsRNA. Thus, the results are in agreement with the general features of reovirus and rotavirus replication where the plus-strand RNAs serve as a template for the synthesis of progeny minus-strands to yield dsRNA (Schonberg, M., et al., *Proc. Natl. Acad. Sci*. Patton, J. T., *Virus Res*., 6, 217–233 (1986); Chen, D., et al., *J. Virol*, 68, 7030–7039 (1994)). However, the semiconservative, strand displacement mechanisms proposed by Spies et al. and Dobos could not be excluded (Spies, U., et al., *Virus Res*., 8, 127–140 (1987); Dobos, P., *Virology*, 208, 10–25 (1995)). The development of a reverse genetics system for IBDV will greatly facilitate future studies of gene expression, pathogenesis, and help in the design of new generations of live and inactivated IBDV vaccines.

As used in the present application, the term "synthetic" as applied to nucleic acids indicates that it is a man made nucleic acid in contrast to a naturally occurring nucleic acid. The term implies no limitation as to the method of manufacture, which can be chemical or biological as long as the method of manufacture involves the intervention of man.

The term "cDNA" is intended to encompass any cDNA containing segments A and B and the 5' and 3' noncoding regions of segments A and B.

The term "infectious" as applied to viruses indicates that the virus has the ability to reproduce. The virus can be pathogenic or nonpathogentic and still be infectious.

The present invention provides a system for the generation of infectious bursal disease virus using synthetic RNA transcripts. This system can be used to study the regulation of viral gene expression, pathogenesis, and for the design of a new generation of live and inactivated IBDV vaccines.

The present invention provides a recombinant vector containing at least one copy of the cDNA according to the present invention. The recombinant vector may also comprise other necessary sequences such as expression control sequences, markers, amplifying genes, signal sequences, promoters, and the like, as is known in the art. Useful vectors for this purpose are plasmids, and viruses such as baculoviruses, herpes virus (HVT) and pox viruses, e.g., fowl pox virus, and the like.

Also provided herein is a host cell transformed with the recombinant vector of the present invention or a host cell transfected with the synthetic RNA of the present invention. The host cell may be a eukaryotic or a prokaryotic host cell. Suitable examples are *E. coli*, insect cell lines such as Sf-9, chicken embryo fibroblast (CEF) cells, chicken embryo kidney (CEK) cells, African green monkey Vero cells and the like.

Also part of this invention is an IBDV poultry vaccine comprising a poultry protecting amount of a recombinantly produced virus or portion of a virus, wherein the virus is inactivated or modified such that it is no longer virulent.

The virus can be inactivated by chemical or physical means. Chemical inactivation can be achieved by treating the virus with, for example, enzymes, formaldehyde, β-propiolactone, ethylene-imine or a derivative thereof, an organic solvent (e.g. halogenated hydrocarbon) and or a detergent. If necessary, the inactivating substance can be neutralized after the virus has been inactivated. Physical inactivation can be carried out by subjecting the viruses to radiation such as UV light, X-radiation, or γ-radiation.

The virus can be attenuated by known methods including serial passage, deleting sequences of nucleic acids and site directed mutagenesis either before or after production of the infectious virus to produce a virus which retains sufficient antigenicity but which has reduced virulence.

Physiologically acceptable carriers for vaccination of poultry are known in the art and need not be further described herein. In addition to being physiologically acceptable to the poultry the carrier must not interfere with the immunological response elicited by the vaccine and/or with the expression of its polypeptide product.

Other additives, such as adjuvants and stabilizers, among others, may also be contained in the vaccine in amounts known in the art. Preferably, adjuvants such as aluminum hydroxide, aluminum phosphate, plant and animal oils, and the like, are administered with the vaccine in amounts sufficient to enhance the immune response to the IBDV. The amount of adjuvant added to the vaccine will vary depending on the nature of the adjuvant, generally ranging from about 0.1 to about 100 times the weight of the IBDV, preferably from about 1 to about 10 times the weight of the IBDV.

The vaccine of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

The vaccine can be administered by any suitable known method of inoculating poultry including nasally, ophthalmically, by injection, in drinking water, in the feed, by exposure, and the like. Preferably, the vaccine is administered by mass administration techniques such as by placing the vaccine in drinking water or by spraying the animals' environment. When administered by injection, the vaccines are preferably administered parenterally. Parenteral administration as used herein means administration by intravenous, subcutaneous, intramuscular, or intraperitoneal injection.

The vaccine of the present invention is administered to poultry to prevent IBD anytime before or after hatching. Preferably, the vaccine is administered prior to the time of birth and after the animal is about 6 weeks of age. Poultry is defined to include but not be limited to chickens, roosters, hens, broilers, roasters, breeders, layers, turkeys and ducks.

The vaccine may be provided in a sterile container in unit form or in other amounts. It is preferably stored frozen, below −20° C., and more preferably below −70° C. It is thawed prior to use, and may be refrozen immediately thereafter. For administration to poultry the recombinantly produced virus may be suspended in a carrier in an amount of about $10^4$ to $10^7$ pfu/ml, and more preferably about $10^5$ to $10^6$ pfu/ml in a carrier such as a saline solution. The inactivated vaccine may contain the antigenic equivalent of $10^4$ to $10^7$ pfu/ml suspended in a carrier. Other carriers may also be utilized as is known in the art. Examples of pharmaceutically acceptable carriers are diluents and inert pharmaceutical carriers known in the art. Preferably, the carrier or diluent is one compatible with the administration of the vaccine by mass administration techniques. However, the carrier or diluent may also be compatible with other administration methods such as injection, eye drops, nose drops, and the like.

The invention also can be used to produce combination vaccines with the IBDV material. The IBDV material can be combined with antigen material of Newcastle Disease Virus Infectious Bronchitis virus, Reo virus, Adeno virus and/or the Marek virus.

The foregoing embodiments of the present invention are further described in the following Examples. However, the present invention is not limited by the Examples, and variations will be apparent to those skilled in the art without departing from the scope of the present invention.

BRIEF DESCRIPTION OF THE DRAWINGS

FIG. 3 shows a comparison of nucleotide sequences of cloned RT-PCR fragments from segments A and B of the chimeric IBDV strain 23A/P2B (bold-typed) with known sequences of segments A and B of serotype II strain 23/82 and serotype I strain P2, respectively. Nucleotide identities are marked by a colon.

EXAMPLES

Viruses and Cells. Two serotype I strains of IBDV, the attenuated P2 strain from Germany and the vaccine strain D78 (Intervet International), and one serotype II strain, the apathogenic 23/82 strain , were propagated in chicken embryo cells (CEC) and purified (Mundt, E. et al., *Virology*, 209, 10–18 (1995); Vakharia, V. N., et al., *Virus Res*., 31, 265–273 (1994)). Vero cells were grown in M199 medium supplemented with 5% fetal calf serum (FCS) and used for transfection experiments. Further propagation of the recovered virus and immunofluorescence studies were carried out in Vero cells (Mundt, E., et al., *J. Gen. Virol*., 76, 437–443, (1995)). For plaque assay, monolayers of secondary CEC were prepared and used (Müller, H., et al., *Virus Res*., 4, 297–309 (1986)).

Figure 1:
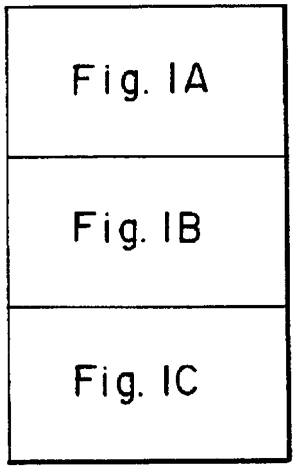
FIG. 1 is a schematic diagram of cDNA constructs used for synthesis of plus-sense ssRNAs of IBDV with T7 RNA polymerase. Construct pUC19FLAD78 contains the cDNA of segment A of IBDV strain D78 and the recombinant plasmid pUC18FLA23 contains the full-length cDNA of segment A of IBDV strain 23/82. Segment A of IBDV encodes the polyprotein (VP2-VP4-VP3), and the recently identified VP5 protein. Plasmid pUC18FLBP2 contains the cDNA of segment B of strain P2 which encodes the RNA-dependent RNA polymerase (VP1). Virus specific sequences are underlined and the T7 promoter sequences are italicized. Restriction sites are shown in boldface and identified. The cleavage sites of the linearized plasmids are shown by vertical arrows and the transcription directions are marked by horizontal arrows.
Figure 4:
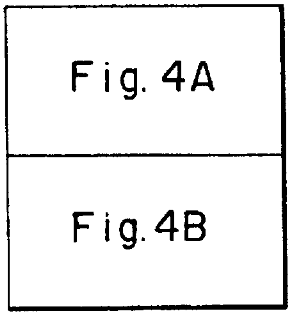
FIG. 4 shows the DNA sequence of pUC18FLA23.
Figure 5:
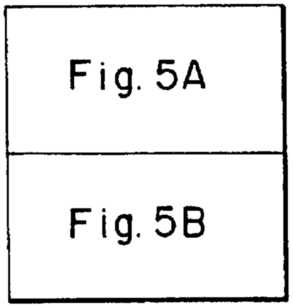
FIG. 5 shows the DNA sequence of pUC19FLAD78.
Figure 6:
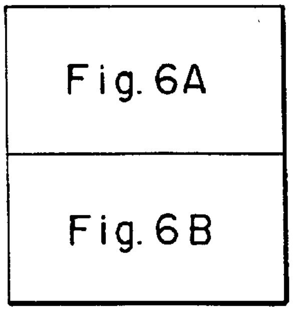
FIG. 6 shows the DNA sequence of pUC18FLBP2.
Figure 1A:
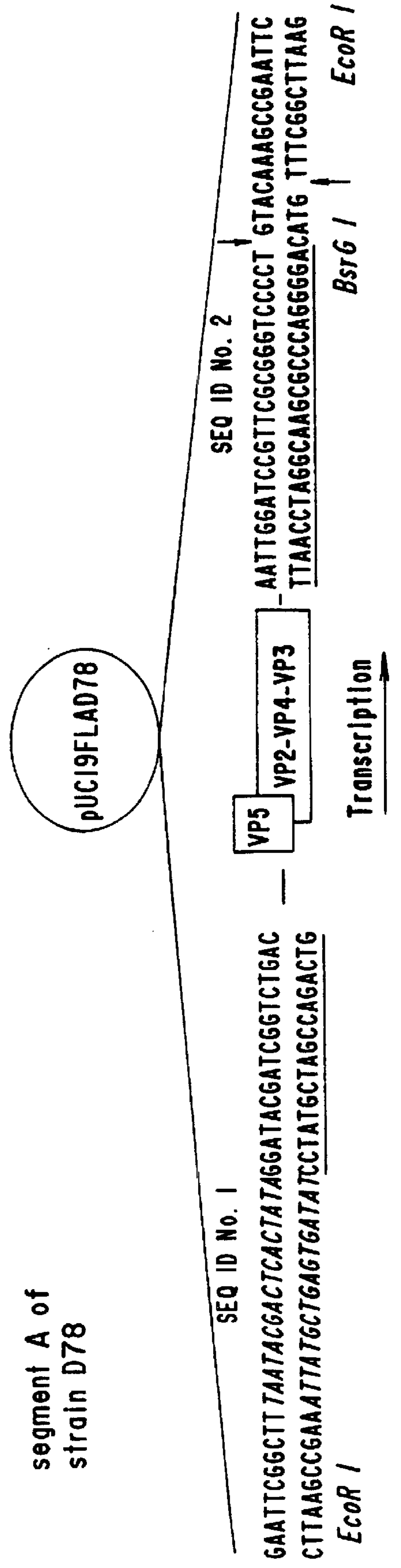
Figure 1B:
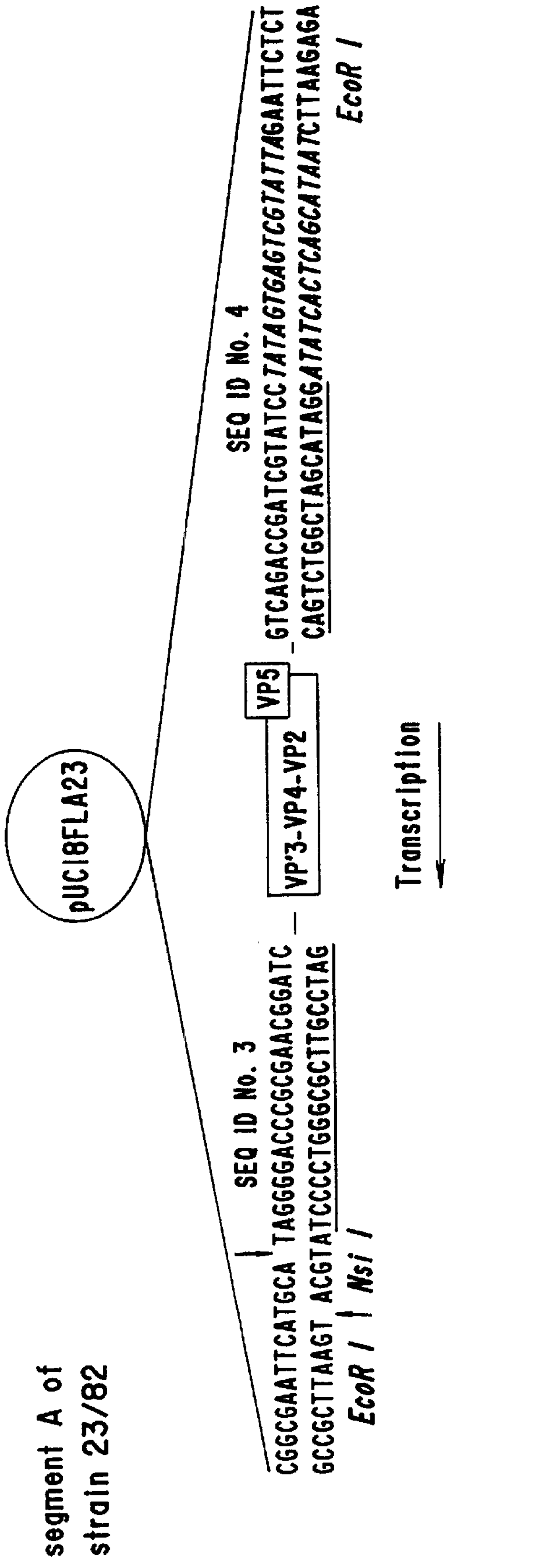
Figure 1C:
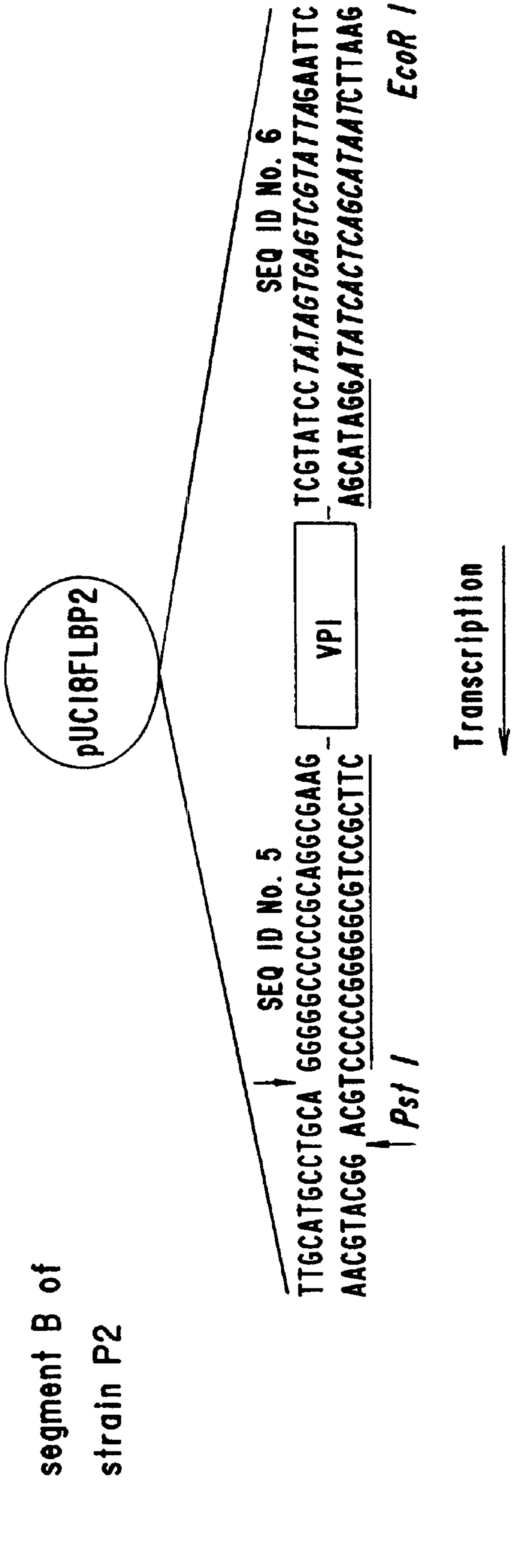

Construction of Full-Length cDNA Clones of IBDV genome. Full-length cDNA clones of IBDV segments A and B were independently prepared. The cDNA clones containing the entire coding region of the RNA segment A of strain D78 were prepared using standard cloning procedures and methods (Vakharia, V. N., et al., *Virus Res*., 31, 265–273 (1994)). By comparing the D78 terminal sequences with recently published terminal sequences of other IBDV strains (Mundt, E. et al., *Virology*, 209, 10–18 (1995)), it was observed that D78 cDNA clones lacked the conserved first 17 and last 10 nucleotides at the 5'- and 3'-ends, respectively. Therefore, to construct a full-length cDNA clone of segment A, two primer pairs (A5'-D78, A5-IPD78 and A3'-IPD78) were synthesized and used for PCR amplification (Table 1). The DNA segments were amplified according to the protocol of the supplier (New England Biolabs) using "Deep Vent Polymerase" (high fidelity thermophilic DNA polymerase). Amplified fragments were cloned into the EcoR I site of a pCRII vector (Invitrogen Corp.) to obtain plasmids pCRD78A5' and pCRD78A3', respectively. Each plasmid was digested with EcoR I and Sal I and the resultant fragments were ligated into EcoR I digested pUC19 to obtain plasmid pUC19FLAD78 (SEQ ID NOS:27 AND 29) which now contains a full-length cDNA copy of segment A encoding all the structural proteins (VP2, VP4 and VP3, SEQ ID NO:30) as well as the non-structural VP5 protein (SEQ ID NO:28) (FIG. 1).

Two primer pairs (A5'-23, A5IP23 and A3'-23, A3-IP23; see Table 1) were used for reverse transcription (RT) of viral genomic dsRNA of strain 23/82 using "SuperScript RT II" (RNA directed DNA polymerase with reduced RNase H activity, GIBCO/BRL). The RT reaction products were purified by phenol/chloroform extraction and ethanol precipitation. To obtain two cDNA fragments bounded by primer pairs A5'-23, A5-IP23 and A3'-23, A3IP23, respectively, RT reaction products were amplified by PCR using "Deep Vent polymerase". Both RT and PCR were carried out according to the supplier's protocol. Resulting PCR fragments were blunt-end ligated into Sma I cleaved pUC18 vector to obtain pUC23A5' and pUC23A3'. The 3'-end of segment A contained in plasmid pUC23A3' was ligated into the Hind III-BstB I cleaved plasmid pUC23A5' to establish the full-length cDNA of segment A of strain 23/82. The resulting plasmid was termed pUC18FLA23 (SEQ ID NOS: 31 AND 33)(FIG. 1) and encodes structural proteins VP2, VP3 and VP4 (SEQ ID NO: 32) and non-structural protein VP5 (SEQ ID NO: 34)

To obtain cDNA clones of segment B of P2 strain, two primer pairs (B5'-P2, B5-IPP2 and B3'-P2, B3-IPP2) were designed according to the published sequences and used for RT-PCR amplification (see Table 1). Using genomic dsRNA as template, cDNA fragments were synthesized and amplified according to the supplier's protocol (Perkin-Elmer Cetus). Amplified fragments were blunt-end ligated into Sma I cleaved pBS vector (Stratagene) to obtain clones pBSP2B5' and pBSP2B3'. To construct a full-length clone of segment B, the 5'-end fragment of plasmid pBSP2B5' was first subcloned between EcoR I and Pst I sites of pUC18 vector to obtain pUCP2B5'. Then the 3'-end fragment of plasmid pBSP2B3' was inserted between the unique Bgl II and Pst I sites of plasmid pUCP2B5' to obtain a full-length plasmid pUC18FLBP2 (SEQ ID NO:25) which encodes the VP1 protein (SEQ ID NO: 26) (FIG. 1). Plasmids pUC18FLBP2, pUC18FLA23 and pUC19FLAD78 were completely sequenced by using the "Sequenase" DNA sequencing system (U.S. Biochem.), and the sequence data were analyzed using either "DNASIS" (Pharmacia) or "PC/Gene" (Intelligenetics) software. The integrity of the full-length constructs was tested by in vitro transcription and translation coupled reticulocyte lysate system using T7 RNA polymerase (Promega).

Transcription and Transfection of Synthetic RNAs. Plasmids pUC19FLAD78, pUC18FLA23 and pUC18FLBP2 were digested with BsrG I, Nsi I and Pst I enzymes (see FIG. 1), respectively, and used as templates for in vitro transcription with T7 RNA polymerase (Promega). Briefly, restriction enzyme cleavage assays were adjusted to 0.5% SDS and incubated with proteinase K (0.5 mg/ml) for 1 hour at 37° C. The linearized DNA templates (~3 $\mu$were recovered after ethanol precipitation, and were added separately to a transcription reaction mixture (50 $\mu$l) containing 40 mM Tris-HCl (pH 7.9), 10 mM NaHCl, 6 mM $MgHCl_2$, 2 mM spermidine, 0.5 mM ATP, CTP and UTP each, 0.1 mM GTP, 0.25 mM cap analog [m7G(5') PPP(5') G], 120 units of "RNasin" (ribonuclease inhibitor), 150 units T7 RNA polymerase (Promega), and incubated at 37° C. for 1 hour. Synthetic RNA transcripts were purified by phenol/chloroform extraction and ethanol precipitation. As controls, the transcription products were treated with either DNase or RNase (Promega) before the purification step.

Vero cells were grown to 80% confluence in 60 mm dishes and washed once with phosphate-buffered saline (PBS). Three ml of "OPTI-MEM I" (reduced serum medium containing HEPES buffer, sodium bicarbonate, hypoxanthine, thymidine, sodium pyruvate, L-glutamine, trace elements, growth factors and phenol red; from GIBCO/BRL) were added to the monolayers, and the cells were incubated at 37° C. for 1 hour in a $CO_2$ incubator. Simultaneously, 0.15 ml of "OPTI-MEM I" was incubated with 1.25 $\mu$g of "Lipofectin" reagent (N-[1-(2,3-dioleyloxy)propyl]-N,N,N-trimethylammonium chloride and dioleoylphosphatidylethanolamine, GIBCO/BRL) for 45 min. in a polystyrene tube at room temperature. Synthetic RNA transcripts of both segments, resuspended in 0.15 ml of diethyl pyrocarbonate-treated water, were added to the OPTI-MEM-Lipofectin-mixture, mixed gently, and incubated on ice for 5 min. After removing the "OPTI-MEM" from the monolayers in 60 mm dishes and replacing with fresh 1.5 ml of "OPTI-MEM", the nucleic acid containing mixture was added drop-wise to the Vero cells and swirled gently. After 2 hours of incubation at 37° C., the mixture was replaced with M199 medium [$CaCl_2$ (annhydrous), $Fe(NO_3)_3$ $9H_2O$, KCl, $MgSO_4$ (anhydrous), NaHCl, $NaH_2PO_4H_2O$, $NaHCO_3$, L-Alanine, L-Arginine HCl, L-Aspartic acid, L-Cysteine HCl $H_2O$, L-Cysteine 2HCl, L-Glutamic acid, L-Glutamine, Glycine, L-Histidine HCL $H_2O$, L-Hydroxyproline, L-Isoleucine, L-Leucine, L-Lysine HCl, L-Methionine, L-Phenylalanine, L-Proline, L-Serine, L-Threonine, L-Tryptophan, L-Tyrosine 2Na $2H_2O$, L-Valine, Alpha tocopherol $PO_4$ $Na_2$, Ascorbic Acid, Biotin, Calciferol, D-Calcium pantothenate, Choline chloride, Folic acid, 1-Inositol, Menandione $NaHSO_3$ $3H_2O$, Niacin, Nicotinamide, Para-aminobenzoic acid, Pyridoxine HCl, Riboflavin, Thiamine HCl, Vitamin A Acetate, Adenine $SO_4$, Adenylic Acid, ATP, $Na_2$, Cholesterol, 2-Deoxy-D-Ribose, D-Glucose, Glutathione, Guanine HCl, Hypoxanthine Na, Phenol Red Na, Ribose, Sodium Acetate (anhydrous), Thymine, Tween 80, Uracil, and Xanthine Na; from Mediatech, Inc.] containing 5% FCS (without rinsing cells) and the cells were further incubated at 37° C. for desired time intervals.

Identification of Generated IBDV. CEC were infected with filtered (0.2 μm) supernatant from Vero cells transfected with transcripts of pUC18FLA23 and pUC18FLP2B. 16 hours post-infection, the whole cell nucleic acids were isolated (Mundt, E. et al., *Virology*, 209, 10–18 (1995)). Primers were designed according to the published sequences and RT-PCR fragments were amplified, cloned and sequenced (Mundt, E. et al., *Virology*, 209, 10–18 (1995)). Sequence data were analyzed by using "DNASIS" software.

Immunofluorescence. Vero cells, grown on cover slips to 80% confluence, were infected with the supernatants derived from transfected Vero cells (after freeze-thawing) and incubated at 37° C. for two days. The cells were then washed, fixed with acetone and treated with polyclonal rabbit anti-IBDV serum. After washing, the cells were treated with fluorescein labeled goat-anti-rabbit antibody (Kirkegaard & Perry Lab.) and examined by fluorescence microscope.

Plaque Assay. Monolayers of secondary CEC, grown in 60 mm dishes, were inoculated with the supernatants derived from transfected Vero cells. After 1 hour of infection, the cells were washed once with PBS and overlayed with 0.8% Agar noble (Difco) containing 10% tryptose phosphate broth, 2% FCS, 0.112% $NaHCO_3$, $10^3$ units penicillin, $10^3$ μg/ml streptomycin, 0.25 μg/ml fungizone, 0.005% neutral red, 0.0015% phenol red. The cells were incubated at 37° C. for 2 to 3 days until plaques could be observed and counted (Müller, H., et al., *Virus Res.*, 4, 297–309 (1986)).

Construction of Full-Length cDNA clones of IBDV Genome. To develop a reverse genetics system for the dsRNA virus IBDV, two independent cDNA clones were constructed that contain segment A of strain D78 and segment B of strain P2 (FIG. 1). Each plasmid encoded either the precursor of structural proteins (VP2, VP4, VP3) and VP5 or only VP1 protein (RNA-dependent RNA polymerase). Plasmid pUC18FLBP2 upon digestion with Pst I and transcription in vitro by T7 RNA polymerase, would yield RNA containing the correct 5'- and 3'-ends. Whereas, upon digestion with BsrG I and transcription, plasmid pUC19FLAD78 would yield RNA containing the correct 5'-end but with additional four nucleotides at the 3'end. Coupled transcription and translation of the above plasmids in a rabbit reticulocyte system yielded protein products that were correctly processed and comigrated with the marker IBDV proteins after fractionating on SDS-polyacrylamide gel and autoradiography (data not shown).

Figure 2:
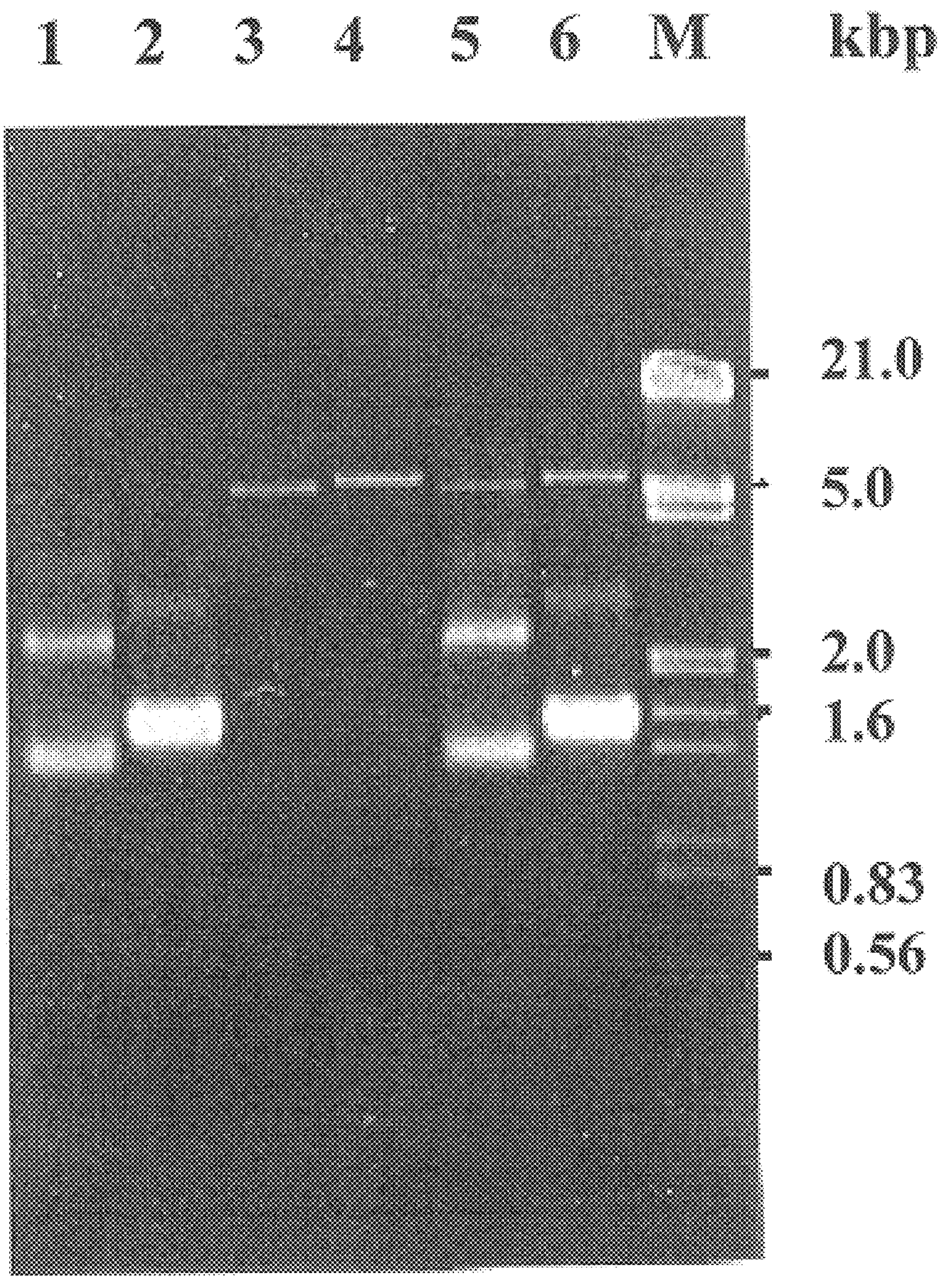
FIG. 2 shows an agarose gel analysis of the transcription reaction products that were used for transfection of Vero cells. Synthetic RNAs transcribed in vitro using T7 RNA polymerase and linearized plasmids pUC19FLAD78 (lanes 2, 4 and 6) containing the cDNA of segment A of IBDV strain D78, and pUC18FLBP2 (lanes 1, 3 and 5) containing the cDNA of segment B of strain P2, respectively. After transcription, the reaction mixtures were either treated with DNase (lanes 1 and 2), RNase (lanes 3 and 4) or left untreated (lanes 5 and 6). Two μl of the reaction products were analyzed on 1% agarose gel. Lambda DNA, digested with Hind III/EcoR I, was used as markers (lane M).

Transcription, Transfection and Generation of Infectious Virus. Plus-sense transcripts of IBDV segment A and B were synthesized separately in vitro with T7 RNA polymerase using linearized full-length cDNA plasmids as templates (see FIG. 2). Although two species of RNA transcripts were observed for segment B on a neutral gel (lanes 1 and 5), fractionation of these samples on a denaturing gel yielded only one transcript-specific band (data not shown). In order to show that plus-sense RNA transcripts of both segments are needed for the generation of infectious virus, the transcription mixtures were incubated with different nucleases, as shown in FIG. 2. Synthetic RNAs recovered after treating the transcription products with DNase (lanes 1+2), RNase (lanes 3+4) or without treatment (lanes 5+6), were used for the transfection of Vero cells. As mock control, Lipofectin alone was used. Five days post-transfection, cytopathic effect (CPE) was only visible in Vero cells transfected with combined transcripts of untreated or DNase-treated transcription products, but not with RNase-treated transcription mixtures or mock-transfected control. In addition, no CPE was detected when Vero cells were transfected with RNA of only segment A or B (data not shown). These results demonstrate that replication of IBDV ensued after transfection of Vero cells with plus-sense ssRNAs of both segments of IBDV. To verify that the agent causing the CPE in Vero cells was indeed IBDV, transfected Vero cells were freeze-thawed, and supematants were clarified by centrifugation, and used to infect CEC or Vero cells. CEC infected with the supernatants derived from Vero transfected cells of untreated or DNase-treated transcription mixtures produced CPE in one day post-inoculation (Table 2). However, no CPE could be detected even after five days in CEC, with the supernatants from transfected Vero cells of RNase-treated transcription mixtures, untreated segment A or B transcription mixtures and mock-transfected Vero cells. Similarly, when Vero cells on cover slips were infected with the same supernatants as described above and examined by immunofluorescence staining after 2 days, only supernatants derived from transfected Vero cells of untreated or DNAse-treated transcription mixtures gave positive immunofluorescence signal (Table 2).

Recovery of Transfectant Virus. To determine the time point for the recovery of infectious virus, Vero cells were transfected with combined RNA transcripts of segments A and B. At 4, 8, 16, 24, 36 and 48 hours post-transfection, the supernatants were examined for the presence of transfectant virus by infectivity and plaque assays, as shown in Table 3. Our results indicate that the virus could be recovered as early as 36 hours after transfection. Virus titer was $2.3\times10^2$ pfu/ml which appear to drop for samples obtained later than 48 hours after transfection.

Generation of a Chimeric Virus. To prove that plus-sense ssRNA of both segments of IBDV are sufficient for recovery of infectious virus, a chimeric IBDV was generated. Plasmid pUC18FLA23 containing a full-length sequence of segment A of serotype II strain was linearized by Nsi I digestion and ssRNA was synthesized in vitro using T7 RNA polymerase. The ssRNA transcript specifies the correct 5'-end but contains one additional residue at the 3'-end (FIG. 1). Vero cells were transfected with ssRNA of segment A of serotype II strain 23/82 and ssRNA of segment B of serotype I strain P2. Five days after transfection when CPE was evident, the supernatant was clarified (after freeze-thawing) and used to infect CEC. After a second passage in CEC, genomic RNA of the virus was analyzed by RT-PCR and sequencing of the PCR products. Primers for segment A were deigned to specifically amplify only segment A sequences derived from the serotype II strain. Primer for segment B bound to sequences of both serotypes. The amplified fragments were cloned and sequenced. The obtained segment A sequences showed a perfect match with known segment A sequences of serotype II strain 23/82, whereas segment B sequence exhibited complete homology to published segment B sequences of serotype I strain P2 (FIG. 3).

TABLE 1

Oligonucleotides Used for the Construction of Full Length cDNA Clones of IBDV Genomic Segments A and B.

| Nucleotide Sequence | Orientation | Name | Nucleotide Number |
|---|---|---|---|
| *TAATACGACTCACTATA*GGATACGATCGGTCTGACCCCGGGGGAGTCA | (+) | A5'-D78 | 1–31 |
| AGA**GAATTC***TAATACGACTCACTATA*GGATACGATCGGTCTGAC | (+) | A5'-23 | 1–48 |
| **TGTACA**GGGGACCCGCGAACGGATCCAATT | (−) | A3'-D78 | 3237–3261 |
| CGGC**GAATTCATGCAT**AGGGGACCCGCGAACGGATC | (−) | A3'-23 | 3242–3261 |
| C**GTCGAC**TACGGGATTCTGG | (−) | A5-IPD78 | 1711–1730 |
| CAGAGGCAGTACTCCGTCTG | (−) | A5-IP23 | 1971–1990 |
| **AGTCGAC**GGGATTCTTGCTT | (+) | A3-IPD78 | 1723–1742 |
| GAAGGTGTGCGAGAGGAC | (+) | A3-IP23 | 1883–1900 |
| AGA**GAATTC***TAATACGACTCACTATA*GGATACGATGGGTCTGAC | (+) | B5'-P2 | 1–18 |
| CGATCTG**CTGCAG**GGGGCCCCCGCAGGCGAAGG | (−) | B3'-P2 | 2807–2827 |
| CTTGAGACTCTTGTTCTCTACTCC | (−) | B5-IPP2 | 1915–1938 |
| ATACAGCAAAGATCTCGGG | (+) | B3-IPP2 | 1839–1857 |

Composition and location of the oligonucleotide primers used for cloning. T7 promoter sequences are marked with italic types, the virus specific sequences are underlined, and the restriction sites marked in boldface. Orientation of the virus specific sequence of the primer is shown for sense (+) and antisense (−). The positions where the primers bind (nucleotide number) are according to the published sequences of P2 strain (2).

TABLE 2

Generation of Infections IBDV From Synthetic RNAs of Segment A and B.

| Material Transfected | CPE | Immunofluoroescence |
|---|---|---|
| ssRNA A + B, DNase-treated | + | + |
| ssRNA A + B, RNase-treated | − | − |
| ssRNA A + B, untreated | + | + |
| ssRNA A, untreated | − | − |
| ssRNA B, untreated | − | − |
| Lipofectin only | − | − |

Vero cells were transfected with synthetic RNAs of segment A and B derived from transcription reactions that were either untreated or treated with DNase or RNase. After 5 days, the supernatants were collected, clarified by centrifugation, and analyzed for the presence of virus. The infectivity of the recovered virus was determined in CEC by the appearance of cytopathic effect (CPE) 1–2 days post-inoculation. The specificity of the recovered virus was determined by immunofluorescence staining of infected Vero cells with rabbit anti-IBDV serum.

TABLE 3

Recovery of Virus at Various Times Post-Transfection.

| Time in hours post-transfection | CPE | Immunofluorescence | pfu/ml |
|---|---|---|---|
| 4 | − | − | 0 |
| 8 | − | − | 0 |
| 16 | − | − | 0 |
| 24 | − | − | 0 |
| 36 | + | + | $2.3 \times 10^2$ |
| 45 | + | + | $6.0 \times 10^1$ |

Vero cell were transfected with synthetic RNAs of segment A and B as described. The infectivity an specificity of the recovered virus was detected by CPE in CEC and immunoflurescence staining in Vero cells, respectively. Monolayers of secondary CEC were used for plaque assay after inoculating the cells with the supernatants derived from transfected Vero cells. Approximate titer of the virus was calculated as plaque forming units per ml (pfu/ml).

What is claimed is:

1. A cDNA containing at least a portion of the Birnavirus genome selected from the group consisting of segment A, segment B and segments A and B, wherein said cDNA includes the 5' and 3' terminii of said segments.

2. The cDNA according to claim 1, wherein said Birnavirus genome is from Infectious Bursal Disease Virus (IBDV) and cDNA is derived from more than one strain of Birnavirus.

3. A recombinant vector comprising at least one copy of a cDNA containing at least a portion of the Birnavirus genome selected from the group consisting of segment A, segment B and segments A and B, wherein said cDNA includes the 5' and 3' terminii of said segments.

4. A synthetic RNA transcribed from a cDNA containing at least a portion of the Birnavirus genome selected from the group consisting of segment A, segment B and segments A and B, wherein said cDNA includes the 5' and 3' terminii of said segments.

5. A host cell transformed with the recombinant vector according to claim 3.

6. A host cell transformed with a synthetic RNA according to claim 4.

7. A live, chimeric Infectious Bursal Disease Virus (IBDV) comprising at least one cDNA of IBDV genome segments A and B, wherein said cDNA is derived from more than one strain of IBDV.

8. A vaccine comprising a live, chimeric IBDV according to claim 7.

9. A method for producing a live Infectious Bursal Disease Virus (IBDV), comprising the following steps:

preparing at least one cDNA of IBDV genome segments A and B, wherein said cDNA is derived from more than one strain of IBDV;

initiating synthesis of a dsRNA in a host cell using RNA derived from said cDNA;

incubating said host cell in a culture medium; and isolating live, IBDV from said culture medium.

10. A synthetic RNA encoding proteins VP1, VP2, VP3, VP4, and VP5 of Infectious Bursal Disease Virus (IBDV), wherein said RNA is derived from more than one strain of IBDV.

11. A host cell transfected with the synthetic RNA according to claim 10.

12. A cDNA containing at least a portion of the Birnavirus genome selected from the group consisting of segment A, segment B and segments A and B of Birnavirus, wherein said cDNA includes the 5' and 3' termini of said segments and said cDNA is derived from more than one strain of Birnavirus.

13. A recombinant vector comprising the cDNA according to claim 12.

14. The vector according to claim 13, where said vector is a plasmid.

15. A host cell transformed with the vector according to claim 14.

* * * * *

SEQUENCE LISTING

```
(1) GENERAL INFORMATION:

   (iii) NUMBER OF SEQUENCES: 34

(2) INFORMATION FOR SEQ ID NO:1:

     (i) SEQUENCE CHARACTERISTICS:
          (A) LENGTH: 46 base pairs
          (B) TYPE: nucleic acid
          (C) STRANDEDNESS: double
          (D) TOPOLOGY: circular

    (ii) MOLECULE TYPE: cDNA

    (xi) SEQUENCE DESCRIPTION: SEQ ID NO:1:

GAATTCGGCT TTAATACGAC TCACTATAGG ATACGATCGG TCTGAC                    46

(2) INFORMATION FOR SEQ ID NO:2:

     (i) SEQUENCE CHARACTERISTICS:
```

-continued (A) LENGTH: 41 base pairs
(B) TYPE: nucleic acid
(C) STRANDEDNESS: double
(D) TOPOLOGY: circular (ii) MOLECULE TYPE: cDNA (xi) SEQUENCE DESCRIPTION: SEQ ID NO:2:

AATTGGATCC GTTCGCGGGT CCCCTGTACA AAGCCGAATT C 41

(2) INFORMATION FOR SEQ ID NO:3:

(i) SEQUENCE CHARACTERISTICS:
(A) LENGTH: 36 base pairs
(B) TYPE: nucleic acid
(C) STRANDEDNESS: double
(D) TOPOLOGY: circular (ii) MOLECULE TYPE: cDNA (xi) SEQUENCE DESCRIPTION: SEQ ID NO:3:

CGGCGAATTC ATGCATAGGG GACCCGCGAA CGGATC 36

(2) INFORMATION FOR SEQ ID NO:4:

(i) SEQUENCE CHARACTERISTICS:
(A) LENGTH: 44 base pairs
(B) TYPE: nucleic acid
(C) STRANDEDNESS: double
(D) TOPOLOGY: circular (ii) MOLECULE TYPE: cDNA (xi) SEQUENCE DESCRIPTION: SEQ ID NO:4:

GTCAGACCGA TCGTATCCTA TAGTGAGTCG TATTAGAATT CTCT 44

(2) INFORMATION FOR SEQ ID NO:5:

(i) SEQUENCE CHARACTERISTICS:
(A) LENGTH: 33 base pairs
(B) TYPE: nucleic acid
(C) STRANDEDNESS: double
(D) TOPOLOGY: circular (ii) MOLECULE TYPE: cDNA (xi) SEQUENCE DESCRIPTION: SEQ ID NO:5:

TTGCATGCCT GCAGGGGGCC CCCGCAGGCG AAG 33

(2) INFORMATION FOR SEQ ID NO:6:

(i) SEQUENCE CHARACTERISTICS:
(A) LENGTH: 31 base pairs
(B) TYPE: nucleic acid
(C) STRANDEDNESS: double
(D) TOPOLOGY: circular (ii) MOLECULE TYPE: cDNA (xi) SEQUENCE DESCRIPTION: SEQ ID NO:6:

TCGTATCCTA TAGTGAGTCG TATTAGAATT C 31

(2) INFORMATION FOR SEQ ID NO:7:

(i) SEQUENCE CHARACTERISTICS:
(A) LENGTH: 120 base pairs
(B) TYPE: nucleic acid
(C) STRANDEDNESS: single
(D) TOPOLOGY: linear -continued (ii) MOLECULE TYPE: DNA (xi) SEQUENCE DESCRIPTION: SEQ ID NO:7:

GGAAGCCTGA GTGAGTTGAC TGACTACAGC TACAACGGGC TGATGTCAGC CACTGCGAAC 60

ATCAACGACA AGATCGGGAA CGTTCTAGTT GGAGAAGGGG TGACTGTTCT CAGTCTACCG 120

(2) INFORMATION FOR SEQ ID NO:8:

(i) SEQUENCE CHARACTERISTICS:
(A) LENGTH: 119 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

GGAAGCCTGA GTGAGTTGAC TGACTACAGC TACAACGGGC TGATGTCAGC CACTGCGAAC 60

ATCAACGACA AGATCGGGAA CGTTCTAGTT GGAGAAGGGG TGACTGTTCT CAGTCTACC 119

(2) INFORMATION FOR SEQ ID NO:9:

(i) SEQUENCE CHARACTERISTICS:
(A) LENGTH: 120 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:9:

GGAAGCCTGA GTGAACTGAC AGATGTTAGC TACAATGGGT TGATGTCTGC AACAGCCAAC 60

ATCAACGACA AAATTGGGAA CGTCCTAGTA GGGGAAGGGG TCACCGTCCT CAGCTTACCC 120

(2) INFORMATION FOR SEQ ID NO:10:

(i) SEQUENCE CHARACTERISTICS:
(A) LENGTH: 120 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:10:

TTTTCAATAG TCCACAGGCG CGAACGAAGA TCTCAGCAGC GTTCGGCATA AAGCCTACTG 60

CTGGACAAGA CGTGGAAGAA CTCTTGATCC CCAAAGTCTG GGTGCCACCT GAGGATCCGC 120

(2) INFORMATION FOR SEQ ID NO:11:

(i) SEQUENCE CHARACTERISTICS:
(A) LENGTH: 120 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

TTTTCAACAG TCCACAGGCG CGAAGCACGA TCTCAGCAGC GTTCGGCATA AAGCCTACTG 60

CTGGACAAGA CGTGGAAGAA CTCTTGATCC CTAAAGTTTG GGTGCCACCT GAGGATCCGC 120

(2) INFORMATION FOR SEQ ID NO:12:

-continued (i) SEQUENCE CHARACTERISTICS:
(A) LENGTH: 120 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

TTTTCAACAG TCCACAGGCG CGAAGCACGA TCTCAGCAGC GTTCGGCATA AAGCCTACTG 60

CTGGACAAGA CGTGGAAGAA CTCTTGATCC CTAAAGTTTG GGTGCCACCT GAGGATCCGC 120

(2) INFORMATION FOR SEQ ID NO:13:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

TAATACGACT CACTATAGGA TACGATCGGT CTGACCCCGG GGGAGTCA 48

(2) INFORMATION FOR SEQ ID NO:14:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

AGAGAATTCT AATACGACTC ACTATAGGAT ACGATCGGTC TGAC 44

(2) INFORMATION FOR SEQ ID NO:15:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:15:

TGTACAGGGG ACCCGCGAAC GGATCCAATT 30

(2) INFORMATION FOR SEQ ID NO:16:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:16:

CGGCGAATTC ATGCATAGGG GACCCGCGAA CGGATC 36

(2) INFORMATION FOR SEQ ID NO:17:

(i) SEQUENCE CHARACTERISTICS:

-continued (A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:17:

CGTCGACTAC GGGATTCTGG 20

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:18:

CAGAGGCAGT ACTCCGTCTG 20

(2) INFORMATION FOR SEQ ID NO:19:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:19:

AGTCGACGGG ATTCTTGCTT 20

(2) INFORMATION FOR SEQ ID NO:20:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:20:

GAAGGTGTGC GAGAGGAC 18

(2) INFORMATION FOR SEQ ID NO:21:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:21:

AGAGAATTCT AATACGACTC ACTATAGGAT ACGATGGGTC TGAC 44

(2) INFORMATION FOR SEQ ID NO:22:

(i) SEQUENCE CHARACTERISTICS:
(A) LENGTH: 33 base pairs
(B) TYPE: nucleic acid
(C) STRANDEDNESS: single
(D) TOPOLOGY: linear -continued (ii) MOLECULE TYPE: DNA (xi) SEQUENCE DESCRIPTION: SEQ ID NO:22:

CGATCTGCTG CAGGGGGCCC CCGCAGGCGA AGG 33

(2) INFORMATION FOR SEQ ID NO:23:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:23:

CTTGAGACTC TTGTTCTCTA CTCC 24

(2) INFORMATION FOR SEQ ID NO:24:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:24:

ATACAGCAAA GATCTCGGG 19

(2) INFORMATION FOR SEQ ID NO:25:

(i) SEQUENCE CHARACTERISTICS:
(A) LENGTH: 2827 base pairs
(B) TYPE: nucleic acid
(C) STRANDEDNESS: single
(D) TOPOLOGY: circular (ii) MOLECULE TYPE: cDNA (ix) FEATURE:
(A) NAME/KEY: CDS
(B) LOCATION: 112..2745

(xi) SEQUENCE DESCRIPTION: SEQ ID NO:25:

```
GGATACGATG GGTCTGACCC TCTGGGAGTC ACGAATTAAC GTGGCTACTA GGGGCGATAC      60

CCGCCGCTGG CCGCCACGTT AGTGGCTCCT CTTCTTGATG ATTCTGCCAC C ATG AGT     117
                                                         Met Ser
                                                           1

GAC ATT TTC AAC AGT CCA CAG GCG CGA AGC ACG ATC TCA GCA GCG TTC      165
Asp Ile Phe Asn Ser Pro Gln Ala Arg Ser Thr Ile Ser Ala Ala Phe
          5                  10                  15

GGC ATA AAG CCT ACT GCT GGA CAA GAC GTG GAA GAA CTC TTG ATC CCT      213
Gly Ile Lys Pro Thr Ala Gly Gln Asp Val Glu Glu Leu Leu Ile Pro
     20                  25                  30

AAA GTT TGG GTG CCA CCT GAG GAT CCG CTT GCC AGC CCT AGT CGA CTG      261
Lys Val Trp Val Pro Pro Glu Asp Pro Leu Ala Ser Pro Ser Arg Leu
 35                  40                  45                  50

GCA AAG TTC CTC AGA GAG AAC GGC TAC AAA GTT TTG CAG CCA CGG TCT      309
Ala Lys Phe Leu Arg Glu Asn Gly Tyr Lys Val Leu Gln Pro Arg Ser
                 55                  60                  65

CTG CCC GAG AAT GAG GAG TAT GAG ACC GAC CAA ATA CTC CCA GAC TTA      357
Leu Pro Glu Asn Glu Glu Tyr Glu Thr Asp Gln Ile Leu Pro Asp Leu
             70                  75                  80
```

-continued

```
GCA TGG ATG CGA CAG ATA GAA GGG GCT GTT TTA AAA CCC ACT CTA TCT      405
Ala Trp Met Arg Gln Ile Glu Gly Ala Val Leu Lys Pro Thr Leu Ser
        85                  90                  95

CTC CCT ATT GGA GAT CAG GAG TAC TTC CCA AAG TAC TAC CCA ACA CAT      453
Leu Pro Ile Gly Asp Gln Glu Tyr Phe Pro Lys Tyr Tyr Pro Thr His
    100                 105                 110

CGC CCT AGC AAG GAG AAG CCC AAT GCG TAC CCG CCA GAC ATC GCA CTA      501
Arg Pro Ser Lys Glu Lys Pro Asn Ala Tyr Pro Pro Asp Ile Ala Leu
115                 120                 125                 130

CTC AAG CAG ATG ATT TAC CTG TTT CTC CAG GTT CCA GAG GCC AAC GAG      549
Leu Lys Gln Met Ile Tyr Leu Phe Leu Gln Val Pro Glu Ala Asn Glu
                135                 140                 145

GGC CTA AAG GAT GAA GTA ACC CTC TTG ACC CAA AAC ATA AGG GAC AAG      597
Gly Leu Lys Asp Glu Val Thr Leu Leu Thr Gln Asn Ile Arg Asp Lys
            150                 155                 160

GCC TAT GGA AGT GGG ACC TAC ATG GGA CAA GCA AAT CGA CTT GTG GCC      645
Ala Tyr Gly Ser Gly Thr Tyr Met Gly Gln Ala Asn Arg Leu Val Ala
        165                 170                 175

ATG AAG GAG GTC GCC ACT GGA AGA AAC CCA AAC AAG GAT CCT CTA AAG      693
Met Lys Glu Val Ala Thr Gly Arg Asn Pro Asn Lys Asp Pro Leu Lys
    180                 185                 190

CTT GGG TAC ACT TTT GAG AGC ATC GCG CAG CTA CTT GAC ATC ACA CTA      741
Leu Gly Tyr Thr Phe Glu Ser Ile Ala Gln Leu Leu Asp Ile Thr Leu
195                 200                 205                 210

CCG GTA GGC CCA CCC GGT GAG GAT GAC AAG CCC TGG GTG CCA CTC ACA      789
Pro Val Gly Pro Pro Gly Glu Asp Asp Lys Pro Trp Val Pro Leu Thr
                215                 220                 225

AGA GTG CCG TCA CGG ATG TTG GTG CTG ACG GGA GAC GTA GAT GGC GAC      837
Arg Val Pro Ser Arg Met Leu Val Leu Thr Gly Asp Val Asp Gly Asp
            230                 235                 240

TTT GAG GTT GAA GAT TAC CTT CCC AAA ATC AAC CTC AAG TCA TCA AGT      885
Phe Glu Val Glu Asp Tyr Leu Pro Lys Ile Asn Leu Lys Ser Ser Ser
        245                 250                 255

GGA CTA CCA TAT GTA GGT CGC ACC AAA GGA GAG ACA ATT GGC GAG ATG      933
Gly Leu Pro Tyr Val Gly Arg Thr Lys Gly Glu Thr Ile Gly Glu Met
    260                 265                 270

ATA GCT ATC TCA AAC CAG TTT CTC AGA GAG CTA TCA ACA CTG TTG AAG      981
Ile Ala Ile Ser Asn Gln Phe Leu Arg Glu Leu Ser Thr Leu Leu Lys
275                 280                 285                 290

CAA GGT GCA GGG ACA AAG GGG TCA AAC AAG AAG AAG CTA CTC AGC ATG     1029
Gln Gly Ala Gly Thr Lys Gly Ser Asn Lys Lys Lys Leu Leu Ser Met
                295                 300                 305

TTA AGT GAC TAT TGG TAC TTA TCA TGC GGG CTT TTG TTT CCA AAG GCT     1077
Leu Ser Asp Tyr Trp Tyr Leu Ser Cys Gly Leu Leu Phe Pro Lys Ala
            310                 315                 320

GAA AGG TAC GAC AAA AGT ACA TGG CTC ACC AAG ACC CGG AAC ATA TGG     1125
Glu Arg Tyr Asp Lys Ser Thr Trp Leu Thr Lys Thr Arg Asn Ile Trp
        325                 330                 335

TCA GCT CCA TCC CCA ACA CAC CTC ATG ATC TCT ATG ATC ACC TGG CCC     1173
Ser Ala Pro Ser Pro Thr His Leu Met Ile Ser Met Ile Thr Trp Pro
    340                 345                 350

GTG ATG TCC AAC AGC CCA AAT AAC GTG TTG AAC ATT GAA GGG TGT CCA     1221
Val Met Ser Asn Ser Pro Asn Asn Val Leu Asn Ile Glu Gly Cys Pro
355                 360                 365                 370

TCA CTC TAC AAA TTC AAC CCG TTC AGA GGA GGG TTG AAC AGG ATC GTC     1269
Ser Leu Tyr Lys Phe Asn Pro Phe Arg Gly Gly Leu Asn Arg Ile Val
                375                 380                 385

GAG TGG ATA TTG GCC CCG GAA GAA CCC AAG GCT CTT GTA TAT GCG GAC     1317
Glu Trp Ile Leu Ala Pro Glu Glu Pro Lys Ala Leu Val Tyr Ala Asp
```

-continued

```
            390                 395                 400

AAC ATA TAC ATT GTC CAC TCA AAC ACG TGG TAC TCA ATT GAC CTA GAG     1365
Asn Ile Tyr Ile Val His Ser Asn Thr Trp Tyr Ser Ile Asp Leu Glu
        405                 410                 415

AAG GGT GAG GCA AAC TGC ACT CGC CAA CAC ATG CAA GCC GCA ATG TAC     1413
Lys Gly Glu Ala Asn Cys Thr Arg Gln His Met Gln Ala Ala Met Tyr
    420                 425                 430

TAC ATA CTC ACC AGA GGG TGG TCA GAC AAC GGC GAC CCA ATG TTC AAT     1461
Tyr Ile Leu Thr Arg Gly Trp Ser Asp Asn Gly Asp Pro Met Phe Asn
435                 440                 445                 450

CAA ACA TGG GCC ACC TTT GCC ATG AAC ATT GCC CCT GCT CTA GTG GTG     1509
Gln Thr Trp Ala Thr Phe Ala Met Asn Ile Ala Pro Ala Leu Val Val
                455                 460                 465

GAC TCA TCG TGC CTG ATA ATG AAC CTG CAA ATT AAG ACC TAT GGT CAA     1557
Asp Ser Ser Cys Leu Ile Met Asn Leu Gln Ile Lys Thr Tyr Gly Gln
            470                 475                 480

GGC AGC GGG AAT GCA GCC ACG TTC ATC AAC AAC CAC CTC TTG AGC ACA     1605
Gly Ser Gly Asn Ala Ala Thr Phe Ile Asn Asn His Leu Leu Ser Thr
        485                 490                 495

CTA GTG CTT GAC CAG TGG AAC CTG ATG AGA CAG CCC AGA CCA GAC AGC     1653
Leu Val Leu Asp Gln Trp Asn Leu Met Arg Gln Pro Arg Pro Asp Ser
    500                 505                 510

GAG GAG TTC AAA TCA ATT GAG GAC AAG CTA GGT ATC AAC TTT AAG ATT     1701
Glu Glu Phe Lys Ser Ile Glu Asp Lys Leu Gly Ile Asn Phe Lys Ile
515                 520                 525                 530

GAG AGG TCC ATT GAT GAT ATC AGG GGC AAG CTG AGA CAG CTT GTC CTC     1749
Glu Arg Ser Ile Asp Asp Ile Arg Gly Lys Leu Arg Gln Leu Val Leu
                535                 540                 545

CTT GCA CAA CCA GGG TAC CTG AGT GGG GGG GTT GAA CCA GAA CAA TCC     1797
Leu Ala Gln Pro Gly Tyr Leu Ser Gly Gly Val Glu Pro Glu Gln Ser
            550                 555                 560

AGC CCA ACT GTT GAG CTT GAC CTA CTA GGG TGG TCA GCT ACA TAC AGC     1845
Ser Pro Thr Val Glu Leu Asp Leu Leu Gly Trp Ser Ala Thr Tyr Ser
        565                 570                 575

AAA GAT CTC GGG ATC TAT GTG CCG GTG CTT GAC AAG GAA CGC CTA TTT     1893
Lys Asp Leu Gly Ile Tyr Val Pro Val Leu Asp Lys Glu Arg Leu Phe
    580                 585                 590

TGT TCT GCT GCG TAT CCC AAG GGA GTA GAG AAC AAG AGT CTC AAG TCC     1941
Cys Ser Ala Ala Tyr Pro Lys Gly Val Glu Asn Lys Ser Leu Lys Ser
595                 600                 605                 610

AAA GTC GGG ATC GAG CAG GCA TAC AAG GTA GTC AGG TAT GAG GCG TTG     1989
Lys Val Gly Ile Glu Gln Ala Tyr Lys Val Val Arg Tyr Glu Ala Leu
                615                 620                 625

AGG TTG GTA GGT GGT TGG AAC TAC CCA CTC CTG AAC AAA GCC TGC AAG     2037
Arg Leu Val Gly Gly Trp Asn Tyr Pro Leu Leu Asn Lys Ala Cys Lys
            630                 635                 640

AAT AAC GCA GGC GCC GCT CGG CGG CAT CTG GAG GCC AAG GGG TTC CCA     2085
Asn Asn Ala Gly Ala Ala Arg Arg His Leu Glu Ala Lys Gly Phe Pro
        645                 650                 655

CTC GAC GAG TTC CTA GCC GAG TGG TCT GAG CTG TCA GAG TTC GGT GAG     2133
Leu Asp Glu Phe Leu Ala Glu Trp Ser Glu Leu Ser Glu Phe Gly Glu
    660                 665                 670

GCC TTC GAA GGC TTC AAT ATC AAG CTG ACC GTA ACA TCT GAG AGC CTA     2181
Ala Phe Glu Gly Phe Asn Ile Lys Leu Thr Val Thr Ser Glu Ser Leu
675                 680                 685                 690

GCC GAA CTG AAC AAG CCA GTA CCC CCC AAG CCC CCA AAT GTC AAC AGA     2229
Ala Glu Leu Asn Lys Pro Val Pro Pro Lys Pro Pro Asn Val Asn Arg
                695                 700                 705

CCA GTC AAC ACT GGG GGA CTC AAG GCA GTC AGC AAC GCC CTC AAG ACC     2277
```

-continued

```
Pro Val Asn Thr Gly Gly Leu Lys Ala Val Ser Asn Ala Leu Lys Thr
            710                 715                 720

GGT CGG TAC AGG AAC GAA GCC GGA CTG AGT GGT CTC GTC CTT CTA GCC      2325
Gly Arg Tyr Arg Asn Glu Ala Gly Leu Ser Gly Leu Val Leu Leu Ala
        725                 730                 735

ACA GCA AGA AGC CGT CTG CAA GAT GCA GTT AAG GCC AAG GCA GAA GCC      2373
Thr Ala Arg Ser Arg Leu Gln Asp Ala Val Lys Ala Lys Ala Glu Ala
    740                 745                 750

GAG AAA CTC CAC AAG TCC AAG CCA GAC GAC CCC GAT GCA GAC TGG TTC      2421
Glu Lys Leu His Lys Ser Lys Pro Asp Asp Pro Asp Ala Asp Trp Phe
755                 760                 765                 770

GAA AGA TCA GAA ACT CTG TCA GAC CTT CTG GAG AAA GCC GAC ATC GCC      2469
Glu Arg Ser Glu Thr Leu Ser Asp Leu Leu Glu Lys Ala Asp Ile Ala
                775                 780                 785

AGC AAG GTC GCC CAC TCA GCA CTC GTG GAA ACA AGC GAC GCC CTT GAA      2517
Ser Lys Val Ala His Ser Ala Leu Val Glu Thr Ser Asp Ala Leu Glu
            790                 795                 800

GCA GTT CAG TCG ACT TCC GTG TAC ACC CCC AAG TAC CCA GAA GTC AAG      2565
Ala Val Gln Ser Thr Ser Val Tyr Thr Pro Lys Tyr Pro Glu Val Lys
        805                 810                 815

AAC CCA CAG ACC GCC TCC AAC CCC GTT GTT GGG CTC CAC CTG CCC GCC      2613
Asn Pro Gln Thr Ala Ser Asn Pro Val Val Gly Leu His Leu Pro Ala
    820                 825                 830

AAG AGA GCC ACC GGT GTC CAG GCC GCT CTT CTC GGA GCA GGA ACG AGC      2661
Lys Arg Ala Thr Gly Val Gln Ala Ala Leu Leu Gly Ala Gly Thr Ser
835                 840                 845                 850

AGA CCA ATG GGG ATG GAG GCC CCA ACA CGG TCC AAG AAC GCC GTG AAA      2709
Arg Pro Met Gly Met Glu Ala Pro Thr Arg Ser Lys Asn Ala Val Lys
                855                 860                 865

ATG GCC AAA CGG CGG CAA CGC CAA AAG GAG AGC CGC TAACAGCCAT           2755
Met Ala Lys Arg Arg Gln Arg Gln Lys Glu Ser Arg
            870                 875

GATGGGAACC ACTCAAGAAG AGGACACTAA TCCCAGACCC CGTATCCCCG GCCTTCGCCT    2815

GCGGGGGCCC CC                                                        2827
```

(2) INFORMATION FOR SEQ ID NO:26:

(i) SEQUENCE CHARACTERISTICS:
(A) LENGTH: 878 amino acids
(B) TYPE: amino acid
(D) TOPOLOGY: linear (ii) MOLECULE TYPE: protein (xi) SEQUENCE DESCRIPTION: SEQ ID NO:26:

```
Met Ser Asp Ile Phe Asn Ser Pro Gln Ala Arg Ser Thr Ile Ser Ala
  1               5                  10                  15

Ala Phe Gly Ile Lys Pro Thr Ala Gly Gln Asp Val Glu Glu Leu Leu
            20                  25                  30

Ile Pro Lys Val Trp Val Pro Pro Glu Asp Pro Leu Ala Ser Pro Ser
        35                  40                  45

Arg Leu Ala Lys Phe Leu Arg Glu Asn Gly Tyr Lys Val Leu Gln Pro
    50                  55                  60

Arg Ser Leu Pro Glu Asn Glu Glu Tyr Glu Thr Asp Gln Ile Leu Pro
 65                  70                  75                  80

Asp Leu Ala Trp Met Arg Gln Ile Glu Gly Ala Val Leu Lys Pro Thr
                 85                  90                  95

Leu Ser Leu Pro Ile Gly Asp Gln Glu Tyr Phe Pro Lys Tyr Tyr Pro
            100                 105                 110
```

-continued

```
Thr His Arg Pro Ser Lys Glu Lys Pro Asn Ala Tyr Pro Pro Asp Ile
        115                 120                 125

Ala Leu Leu Lys Gln Met Ile Tyr Leu Phe Leu Gln Val Pro Glu Ala
    130                 135                 140

Asn Glu Gly Leu Lys Asp Glu Val Thr Leu Leu Thr Gln Asn Ile Arg
145                 150                 155                 160

Asp Lys Ala Tyr Gly Ser Gly Thr Tyr Met Gly Gln Ala Asn Arg Leu
                165                 170                 175

Val Ala Met Lys Glu Val Ala Thr Gly Arg Asn Pro Asn Lys Asp Pro
            180                 185                 190

Leu Lys Leu Gly Tyr Thr Phe Glu Ser Ile Ala Gln Leu Leu Asp Ile
        195                 200                 205

Thr Leu Pro Val Gly Pro Pro Gly Glu Asp Asp Lys Pro Trp Val Pro
    210                 215                 220

Leu Thr Arg Val Pro Ser Arg Met Leu Val Leu Thr Gly Asp Val Asp
225                 230                 235                 240

Gly Asp Phe Glu Val Glu Asp Tyr Leu Pro Lys Ile Asn Leu Lys Ser
                245                 250                 255

Ser Ser Gly Leu Pro Tyr Val Gly Arg Thr Lys Gly Glu Thr Ile Gly
            260                 265                 270

Glu Met Ile Ala Ile Ser Asn Gln Phe Leu Arg Glu Leu Ser Thr Leu
        275                 280                 285

Leu Lys Gln Gly Ala Gly Thr Lys Gly Ser Asn Lys Lys Lys Leu Leu
    290                 295                 300

Ser Met Leu Ser Asp Tyr Trp Tyr Leu Ser Cys Gly Leu Leu Phe Pro
305                 310                 315                 320

Lys Ala Glu Arg Tyr Asp Lys Ser Thr Trp Leu Thr Lys Thr Arg Asn
                325                 330                 335

Ile Trp Ser Ala Pro Ser Pro Thr His Leu Met Ile Ser Met Ile Thr
            340                 345                 350

Trp Pro Val Met Ser Asn Ser Pro Asn Asn Val Leu Asn Ile Glu Gly
        355                 360                 365

Cys Pro Ser Leu Tyr Lys Phe Asn Pro Phe Arg Gly Gly Leu Asn Arg
    370                 375                 380

Ile Val Glu Trp Ile Leu Ala Pro Glu Glu Pro Lys Ala Leu Val Tyr
385                 390                 395                 400

Ala Asp Asn Ile Tyr Ile Val His Ser Asn Thr Trp Tyr Ser Ile Asp
                405                 410                 415

Leu Glu Lys Gly Glu Ala Asn Cys Thr Arg Gln His Met Gln Ala Ala
            420                 425                 430

Met Tyr Tyr Ile Leu Thr Arg Gly Trp Ser Asp Asn Gly Asp Pro Met
        435                 440                 445

Phe Asn Gln Thr Trp Ala Thr Phe Ala Met Asn Ile Ala Pro Ala Leu
    450                 455                 460

Val Val Asp Ser Ser Cys Leu Ile Met Asn Leu Gln Ile Lys Thr Tyr
465                 470                 475                 480

Gly Gln Gly Ser Gly Asn Ala Ala Thr Phe Ile Asn Asn His Leu Leu
                485                 490                 495

Ser Thr Leu Val Leu Asp Gln Trp Asn Leu Met Arg Gln Pro Arg Pro
            500                 505                 510

Asp Ser Glu Glu Phe Lys Ser Ile Glu Asp Lys Leu Gly Ile Asn Phe
        515                 520                 525
```

-continued

```
Lys Ile Glu Arg Ser Ile Asp Asp Ile Arg Gly Lys Leu Arg Gln Leu
    530                 535                 540

Val Leu Leu Ala Gln Pro Gly Tyr Leu Ser Gly Gly Val Glu Pro Glu
545                 550                 555                 560

Gln Ser Ser Pro Thr Val Glu Leu Asp Leu Leu Gly Trp Ser Ala Thr
                565                 570                 575

Tyr Ser Lys Asp Leu Gly Ile Tyr Val Pro Val Leu Asp Lys Glu Arg
            580                 585                 590

Leu Phe Cys Ser Ala Ala Tyr Pro Lys Gly Val Glu Asn Lys Ser Leu
        595                 600                 605

Lys Ser Lys Val Gly Ile Glu Gln Ala Tyr Lys Val Val Arg Tyr Glu
    610                 615                 620

Ala Leu Arg Leu Val Gly Gly Trp Asn Tyr Pro Leu Leu Asn Lys Ala
625                 630                 635                 640

Cys Lys Asn Asn Ala Gly Ala Ala Arg Arg His Leu Glu Ala Lys Gly
                645                 650                 655

Phe Pro Leu Asp Glu Phe Leu Ala Glu Trp Ser Glu Leu Ser Glu Phe
            660                 665                 670

Gly Glu Ala Phe Glu Gly Phe Asn Ile Lys Leu Thr Val Thr Ser Glu
        675                 680                 685

Ser Leu Ala Glu Leu Asn Lys Pro Val Pro Pro Lys Pro Pro Asn Val
    690                 695                 700

Asn Arg Pro Val Asn Thr Gly Gly Leu Lys Ala Val Ser Asn Ala Leu
705                 710                 715                 720

Lys Thr Gly Arg Tyr Arg Asn Glu Ala Gly Leu Ser Gly Leu Val Leu
                725                 730                 735

Leu Ala Thr Ala Arg Ser Arg Leu Gln Asp Ala Val Lys Ala Lys Ala
            740                 745                 750

Glu Ala Glu Lys Leu His Lys Ser Lys Pro Asp Asp Pro Asp Ala Asp
        755                 760                 765

Trp Phe Glu Arg Ser Glu Thr Leu Ser Asp Leu Leu Glu Lys Ala Asp
    770                 775                 780

Ile Ala Ser Lys Val Ala His Ser Ala Leu Val Glu Thr Ser Asp Ala
785                 790                 795                 800

Leu Glu Ala Val Gln Ser Thr Ser Val Tyr Thr Pro Lys Tyr Pro Glu
                805                 810                 815

Val Lys Asn Pro Gln Thr Ala Ser Asn Pro Val Val Gly Leu His Leu
            820                 825                 830

Pro Ala Lys Arg Ala Thr Gly Val Gln Ala Ala Leu Leu Gly Ala Gly
        835                 840                 845

Thr Ser Arg Pro Met Gly Met Glu Ala Pro Thr Arg Ser Lys Asn Ala
    850                 855                 860

Val Lys Met Ala Lys Arg Arg Gln Arg Gln Lys Glu Ser Arg
865                 870                 875
```

(2) INFORMATION FOR SEQ ID NO:27:

(i) SEQUENCE CHARACTERISTICS:
(A) LENGTH: 3261 base pairs
(B) TYPE: nucleic acid
(C) STRANDEDNESS: single
(D) TOPOLOGY: circular (ii) MOLECULE TYPE: cDNA (ix) FEATURE:
(A) NAME/KEY: CDS -continued (B) LOCATION: 97..531

(xi) SEQUENCE DESCRIPTION: SEQ ID NO:27:

```
GGATACGATC GGTCTGACCC CGGGGGAGTC ACCCGGGGAC AGGCCGTCAA GGCCTTGTTC     60

CAGGATGGGA CTCCTCCTTC TACAACGCTA TCATTG ATG GTT AGT AGA GAT CAG      114
                                        Met Val Ser Arg Asp Gln
                                            880

ACA AAC GAT CGC AGC GAT GAC AAA CCT GCA AGA TCA AAC CCA ACA GAT      162
Thr Asn Asp Arg Ser Asp Asp Lys Pro Ala Arg Ser Asn Pro Thr Asp
885                 890                 895                 900

TGT TCC GTT CAT ACG GAG CCT TCT GAT GCC AAC AAC CGG ACC GGC GTC      210
Cys Ser Val His Thr Glu Pro Ser Asp Ala Asn Asn Arg Thr Gly Val
                905                 910                 915

CAT TCC GGA CGA CAC CCT GGA GAA GCA CAC TCT CAG GTC AGA GAC CTC      258
His Ser Gly Arg His Pro Gly Glu Ala His Ser Gln Val Arg Asp Leu
            920                 925                 930

GAC CTA CAA TTT GAC TGT GGG GGA CAC AGG GTC AGG GCT AAT TGT CTT      306
Asp Leu Gln Phe Asp Cys Gly Gly His Arg Val Arg Ala Asn Cys Leu
        935                 940                 945

TTT CCC TGG ATT CCC TGG CTC AAT TGT GGG TGC TCA CTA CAC ACT GCA      354
Phe Pro Trp Ile Pro Trp Leu Asn Cys Gly Cys Ser Leu His Thr Ala
    950                 955                 960

GGG CAA TGG GAA CTA CAA GTT CGA TCA GAT GCT CCT GAC TGC CCA GAA      402
Gly Gln Trp Glu Leu Gln Val Arg Ser Asp Ala Pro Asp Cys Pro Glu
965                 970                 975                 980

CCT ACC GGC CAG TTA CAA CTA CTG CAG GCT AGT GAG TCG GAG TCT CAC      450
Pro Thr Gly Gln Leu Gln Leu Leu Gln Ala Ser Glu Ser Glu Ser His
                985                 990                 995

AGT GAG GTC AAG CAC ACT TCC TGG TGG CGT TTA TGC ACT AAA CGG CAC      498
Ser Glu Val Lys His Thr Ser Trp Trp Arg Leu Cys Thr Lys Arg His
            1000                1005                1010

CAT AAA CGC CGT GAC CTT CCA AGG AAG CCT GAG TGAACTGACA GATGTTAGCT    551
His Lys Arg Arg Asp Leu Pro Arg Lys Pro Glu
        1015                1020

ACAATGGGTT GATGTCTGCA ACAGCCAACA TCAACGACAA AATTGGGAAC GTCCTAGTAG    611

GGGAAGGGGT CACCGTCCTC AGCTTACCCA CATCATATGA TCTTGGGTAT GTGAGGCTTG    671

GTGACCCCAT TCCCGCAATA GGGCTTGACC CAAAAATGGT AGCCACATGT GACAGCAGTG    731

ACAGGCCCAG AGTCTACACC ATAACTGCAG CCGATGATTA CCAATTCTCA TCACAGTACC    791

AACCAGGTGG GGTAACAATC ACACTGTTCT CAGCCAACAT TGATGCCATC ACAAGCCTCA    851

GCGTTGGGGG AGAGCTCGTG TTTCAAACAA GCGTCCACGG CCTTGTACTG GGCGCCACCA    911

TCTACCTCAT AGGCTTTGAT GGGACAACGG TAATCACCAG GGCTGTGGCC GCAAACAATG    971

GGCTGACGAC CGGCACCGAC AACCTTATGC CATTCAATCT TGTGATTCCA ACAAACGAGA   1031

TAACCCAGCC AATCACATCC ATCAAACTGG AGATAGTGAC CTCCAAAAGT GGTGGTCAGG   1091

CAGGGGATCA GATGTCATGG TCGGCAAGAG GGAGCCTAGC AGTGACGATC CATGGTGGCA   1151

ACTATCCAGG GGCCCTCCGT CCCGTCACGC TAGTGGCCTA CGAAAGAGTG GCAACAGGAT   1211

CCGTCGTTAC GGTCGCTGGG GTGAGCAACT TCGAGCTGAT CCCAAATCCT GAACTAGCAA   1271

AGAACCTGGT TACAGAATAC GGCCGATTTG ACCCAGGAGC CATGAACTAC ACAAAATTGA   1331

TACTGAGTGA GAGGGACCGT CTTGGCATCA AGACCGTCTG GCCAACAAGG GAGTACACTG   1391

ACTTTCGTGA ATACTTCATG GAGGTGGCCG ACCTCAACTC TCCCCTGAAG ATTGCAGGAG   1451

CATTCGGCTT CAAAGACATA ATCCGGGCCA TAAGGAGGAT AGCTGTGCCG GTGGTCTCCA   1511

CATTGTTCCC ACCTGCCGCT CCCCTAGCCC ATGCAATTGG GGAAGGTGTA GACTACCTGC   1571
```

-continued

TGGGCGATGA GGCACAGGCT GCTTCAGGAA CTGCTCGAGC CGCGTCAGGA AAAGCAAGAG 1631

CTGCCTCAGG CCGCATAAGG CAGCTGACTC TCGCCGCCGA CAAGGGGTAC GAGGTAGTCG 1691

CGAATCTATT CCAGGTGCCC CAGAATCCCG TAGTCGACGG GATTCTTGCT TCACCTGGGG 1751

TACTCCGCGG TGCACACAAC CTCGACTGCG TGTTAAGAGA GGGTGCCACG CTATTCCCTG 1811

TGGTTATTAC GACAGTGGAA GACGCCATGA CACCCAAAGC ATTGAACAGC AAAATGTTTG 1871

CTGTCATTGA AGGCGTGCGA GAAGACCTCC AACCTCCATC TCAAAGAGGA TCCTTCATAC 1931

GAACTCTCTC TGGACACAGA GTCTATGGAT ATGCTCCAGA TGGGGTACTT CCACTGGAGA 1991

CTGGGAGAGA CTACACCGTT GTCCCAATAG ATGATGTCTG GGACGACAGC ATTATGCTGT 2051

CCAAAGATCC CATACCTCCT ATTGTGGGAA ACAGTGGAAA TCTAGCCATA GCTTACATGG 2111

ATGTGTTTCG ACCCAAAGTC CCAATCCATG TGGCTATGAC GGGAGCCCTC AATGCTTGTG 2171

GCGAGATTGA GAAAGTAAGC TTTAGAAGCA CCAAGCTCGC CACTGCACAC CGACTTGGCC 2231

TTAGGTTGGC TGGTCCCGGA GCATTCGATG TAAACACCGG GCCCAACTGG GCAACGTTCA 2291

TCAAACGTTT CCCTCACAAT CCACGCGACT GGGACAGGCT CCCCTACCTC AACCTACCAT 2351

ACCTTCCACC CAATGCAGGA CGCCAGTACC ACCTTGCCAT GGCTGCATCA GAGTTCAAAG 2411

AGACCCCCGA ACTCGAGAGT GCCGTCAGAG CAATGGAAGC AGCAGCCAAC GTGGACCCAC 2471

TATTCCAATC TGCACTCAGT GTGTTCATGT GGCTGGAAGA GAATGGGATT GTGACTGACA 2531

TGGCCAACTT CGCACTCAGC GACCCGAACG CCCATCGGAT GCGAAATTTT CTTGCAAACG 2591

CACCACAAGC AGGCAGCAAG TCGCAAAGGG CCAAGTACGG GACAGCAGGC TACGGAGTGG 2651

AGGCTCGGGG CCCCACACCA GAGGAAGCAC AGAGGGAAAA AGACACACGG ATCTCAAAGA 2711

AGATGGAGAC CATGGGCATC TACTTTGCAA CACCAGAATG GGTAGCACTC AATGGGCACC 2771

GAGGGCCAAG CCCCGGCCAG CTAAAGTACT GGCAGAACAC ACGAGAAATA CCGGACCCAA 2831

ACGAGGACTA TCTAGACTAC GTGCATGCAG AGAAGAGCCG GTTGGCATCA GAAGAACAAA 2891

TCCTAAGGGC AGCTACGTCG ATCTACGGGG CTCCAGGACA GGCAGAGCCA CCCCAAGCTT 2951

TCATAGACGA AGTTGCCAAA GTCTATGAAA TCAACCATGG ACGTGGCCCA AACCAAGAAC 3011

AGATGAAAGA TCTGCTCTTG ACTGCGATGG AGATGAAGCA TCGCAATCCC AGGCGGGCTC 3071

TACCAAAGCC CAAGCCAAAA CCCAATGCTC CAACACAGAG ACCCCCTGGT CGGCTGGGCC 3131

GCTGGATCAG GACCGTCTCT GATGAGGACC TTGAGTGAGG CTCCTGGGAG TCTCCCGACA 3191

CCACCCGCGC AGGTGTGGAC ACCAATTCGG CCTTACAACA TCCCAAATTG GATCCGTTCG 3251

CGGGTCCCCT 3261

(2) INFORMATION FOR SEQ ID NO:28:

(i) SEQUENCE CHARACTERISTICS:
(A) LENGTH: 145 amino acids
(B) TYPE: amino acid
(D) TOPOLOGY: linear (ii) MOLECULE TYPE: protein (xi) SEQUENCE DESCRIPTION: SEQ ID NO:28:

Met Val Ser Arg Asp Gln Thr Asn Asp Arg Ser Asp Asp Lys Pro Ala
1 5 10 15

Arg Ser Asn Pro Thr Asp Cys Ser Val His Thr Glu Pro Ser Asp Ala
20 25 30

Asn Asn Arg Thr Gly Val His Ser Gly Arg His Pro Gly Glu Ala His
35 40 45

-continued

Ser Gln Val Arg Asp Leu Asp Leu Gln Phe Asp Cys Gly Gly His Arg
50 55 60

Val Arg Ala Asn Cys Leu Phe Pro Trp Ile Pro Trp Leu Asn Cys Gly
65 70 75 80

Cys Ser Leu His Thr Ala Gly Gln Trp Glu Leu Gln Val Arg Ser Asp
85 90 95

Ala Pro Asp Cys Pro Glu Pro Thr Gly Gln Leu Gln Leu Leu Gln Ala
100 105 110

Ser Glu Ser Glu Ser His Ser Glu Val Lys His Thr Ser Trp Trp Arg
115 120 125

Leu Cys Thr Lys Arg His His Lys Arg Arg Asp Leu Pro Arg Lys Pro
130 135 140

Glu
145

(2) INFORMATION FOR SEQ ID NO:29:

(i) SEQUENCE CHARACTERISTICS:
(A) LENGTH: 3261 base pairs
(B) TYPE: nucleic acid
(C) STRANDEDNESS: single
(D) TOPOLOGY: circular (ii) MOLECULE TYPE: cDNA (ix) FEATURE:
(A) NAME/KEY: CDS
(B) LOCATION: 131..3166

(xi) SEQUENCE DESCRIPTION: SEQ ID NO:29:

GGATACGATC GGTCTGACCC CGGGGGAGTC ACCCGGGGAC AGGCCGTCAA GGCCTTGTTC 60

CAGGATGGGA CTCCTCCTTC TACAACGCTA TCATTGATGG TTAGTAGAGA TCAGACAAAC 120

GATCGCAGCG ATG ACA AAC CTG CAA GAT CAA ACC CAA CAG ATT GTT CCG 169
Met Thr Asn Leu Gln Asp Gln Thr Gln Gln Ile Val Pro
150 155

TTC ATA CGG AGC CTT CTG ATG CCA ACA ACC GGA CCG GCG TCC ATT CCG 217
Phe Ile Arg Ser Leu Leu Met Pro Thr Thr Gly Pro Ala Ser Ile Pro
160 165 170

GAC GAC ACC CTG GAG AAG CAC ACT CTC AGG TCA GAG ACC TCG ACC TAC 265
Asp Asp Thr Leu Glu Lys His Thr Leu Arg Ser Glu Thr Ser Thr Tyr
175 180 185 190

AAT TTG ACT GTG GGG GAC ACA GGG TCA GGG CTA ATT GTC TTT TTC CCT 313
Asn Leu Thr Val Gly Asp Thr Gly Ser Gly Leu Ile Val Phe Phe Pro
195 200 205

GGA TTC CCT GGC TCA ATT GTG GGT GCT CAC TAC ACA CTG CAG GGC AAT 361
Gly Phe Pro Gly Ser Ile Val Gly Ala His Tyr Thr Leu Gln Gly Asn
210 215 220

GGG AAC TAC AAG TTC GAT CAG ATG CTC CTG ACT GCC CAG AAC CTA CCG 409
Gly Asn Tyr Lys Phe Asp Gln Met Leu Leu Thr Ala Gln Asn Leu Pro
225 230 235

GCC AGT TAC AAC TAC TGC AGG CTA GTG AGT CGG AGT CTC ACA GTG AGG 457
Ala Ser Tyr Asn Tyr Cys Arg Leu Val Ser Arg Ser Leu Thr Val Arg
240 245 250

TCA AGC ACA CTT CCT GGT GGC GTT TAT GCA CTA AAC GGC ACC ATA AAC 505
Ser Ser Thr Leu Pro Gly Gly Val Tyr Ala Leu Asn Gly Thr Ile Asn
255 260 265 270

GCC GTG ACC TTC CAA GGA AGC CTG AGT GAA CTG ACA GAT GTT AGC TAC 553
Ala Val Thr Phe Gln Gly Ser Leu Ser Glu Leu Thr Asp Val Ser Tyr
275 280 285

-continued

```
AAT GGG TTG ATG TCT GCA ACA GCC AAC ATC AAC GAC AAA ATT GGG AAC      601
Asn Gly Leu Met Ser Ala Thr Ala Asn Ile Asn Asp Lys Ile Gly Asn
            290                 295                 300

GTC CTA GTA GGG GAA GGG GTC ACC GTC CTC AGC TTA CCC ACA TCA TAT      649
Val Leu Val Gly Glu Gly Val Thr Val Leu Ser Leu Pro Thr Ser Tyr
        305                 310                 315

GAT CTT GGG TAT GTG AGG CTT GGT GAC CCC ATT CCC GCA ATA GGG CTT      697
Asp Leu Gly Tyr Val Arg Leu Gly Asp Pro Ile Pro Ala Ile Gly Leu
    320                 325                 330

GAC CCA AAA ATG GTA GCC ACA TGT GAC AGC AGT GAC AGG CCC AGA GTC      745
Asp Pro Lys Met Val Ala Thr Cys Asp Ser Ser Asp Arg Pro Arg Val
335                 340                 345                 350

TAC ACC ATA ACT GCA GCC GAT GAT TAC CAA TTC TCA TCA CAG TAC CAA      793
Tyr Thr Ile Thr Ala Ala Asp Asp Tyr Gln Phe Ser Ser Gln Tyr Gln
                355                 360                 365

CCA GGT GGG GTA ACA ATC ACA CTG TTC TCA GCC AAC ATT GAT GCC ATC      841
Pro Gly Gly Val Thr Ile Thr Leu Phe Ser Ala Asn Ile Asp Ala Ile
            370                 375                 380

ACA AGC CTC AGC GTT GGG GGA GAG CTC GTG TTT CAA ACA AGC GTC CAC      889
Thr Ser Leu Ser Val Gly Gly Glu Leu Val Phe Gln Thr Ser Val His
        385                 390                 395

GGC CTT GTA CTG GGC GCC ACC ATC TAC CTC ATA GGC TTT GAT GGG ACA      937
Gly Leu Val Leu Gly Ala Thr Ile Tyr Leu Ile Gly Phe Asp Gly Thr
    400                 405                 410

ACG GTA ATC ACC AGG GCT GTG GCC GCA AAC AAT GGG CTG ACG ACC GGC      985
Thr Val Ile Thr Arg Ala Val Ala Ala Asn Asn Gly Leu Thr Thr Gly
415                 420                 425                 430

ACC GAC AAC CTT ATG CCA TTC AAT CTT GTG ATT CCA ACA AAC GAG ATA     1033
Thr Asp Asn Leu Met Pro Phe Asn Leu Val Ile Pro Thr Asn Glu Ile
                435                 440                 445

ACC CAG CCA ATC ACA TCC ATC AAA CTG GAG ATA GTG ACC TCC AAA AGT     1081
Thr Gln Pro Ile Thr Ser Ile Lys Leu Glu Ile Val Thr Ser Lys Ser
            450                 455                 460

GGT GGT CAG GCA GGG GAT CAG ATG TCA TGG TCG GCA AGA GGG AGC CTA     1129
Gly Gly Gln Ala Gly Asp Gln Met Ser Trp Ser Ala Arg Gly Ser Leu
        465                 470                 475

GCA GTG ACG ATC CAT GGT GGC AAC TAT CCA GGG GCC CTC CGT CCC GTC     1177
Ala Val Thr Ile His Gly Gly Asn Tyr Pro Gly Ala Leu Arg Pro Val
    480                 485                 490

ACG CTA GTG GCC TAC GAA AGA GTG GCA ACA GGA TCC GTC GTT ACG GTC     1225
Thr Leu Val Ala Tyr Glu Arg Val Ala Thr Gly Ser Val Val Thr Val
495                 500                 505                 510

GCT GGG GTG AGC AAC TTC GAG CTG ATC CCA AAT CCT GAA CTA GCA AAG     1273
Ala Gly Val Ser Asn Phe Glu Leu Ile Pro Asn Pro Glu Leu Ala Lys
                515                 520                 525

AAC CTG GTT ACA GAA TAC GGC CGA TTT GAC CCA GGA GCC ATG AAC TAC     1321
Asn Leu Val Thr Glu Tyr Gly Arg Phe Asp Pro Gly Ala Met Asn Tyr
            530                 535                 540

ACA AAA TTG ATA CTG AGT GAG AGG GAC CGT CTT GGC ATC AAG ACC GTC     1369
Thr Lys Leu Ile Leu Ser Glu Arg Asp Arg Leu Gly Ile Lys Thr Val
        545                 550                 555

TGG CCA ACA AGG GAG TAC ACT GAC TTT CGT GAA TAC TTC ATG GAG GTG     1417
Trp Pro Thr Arg Glu Tyr Thr Asp Phe Arg Glu Tyr Phe Met Glu Val
    560                 565                 570

GCC GAC CTC AAC TCT CCC CTG AAG ATT GCA GGA GCA TTC GGC TTC AAA     1465
Ala Asp Leu Asn Ser Pro Leu Lys Ile Ala Gly Ala Phe Gly Phe Lys
575                 580                 585                 590

GAC ATA ATC CGG GCC ATA AGG AGG ATA GCT GTG CCG GTG GTC TCC ACA     1513
Asp Ile Ile Arg Ala Ile Arg Arg Ile Ala Val Pro Val Val Ser Thr
                595                 600                 605
```

-continued

```
TTG TTC CCA CCT GCC GCT CCC CTA GCC CAT GCA ATT GGG GAA GGT GTA     1561
Leu Phe Pro Pro Ala Ala Pro Leu Ala His Ala Ile Gly Glu Gly Val
            610                 615                 620

GAC TAC CTG CTG GGC GAT GAG GCA CAG GCT GCT TCA GGA ACT GCT CGA     1609
Asp Tyr Leu Leu Gly Asp Glu Ala Gln Ala Ala Ser Gly Thr Ala Arg
        625                 630                 635

GCC GCG TCA GGA AAA GCA AGA GCT GCC TCA GGC CGC ATA AGG CAG CTG     1657
Ala Ala Ser Gly Lys Ala Arg Ala Ala Ser Gly Arg Ile Arg Gln Leu
    640                 645                 650

ACT CTC GCC GCC GAC AAG GGG TAC GAG GTA GTC GCG AAT CTA TTC CAG     1705
Thr Leu Ala Ala Asp Lys Gly Tyr Glu Val Val Ala Asn Leu Phe Gln
655                 660                 665                 670

GTG CCC CAG AAT CCC GTA GTC GAC GGG ATT CTT GCT TCA CCT GGG GTA     1753
Val Pro Gln Asn Pro Val Val Asp Gly Ile Leu Ala Ser Pro Gly Val
                675                 680                 685

CTC CGC GGT GCA CAC AAC CTC GAC TGC GTG TTA AGA GAG GGT GCC ACG     1801
Leu Arg Gly Ala His Asn Leu Asp Cys Val Leu Arg Glu Gly Ala Thr
            690                 695                 700

CTA TTC CCT GTG GTT ATT ACG ACA GTG GAA GAC GCC ATG ACA CCC AAA     1849
Leu Phe Pro Val Val Ile Thr Thr Val Glu Asp Ala Met Thr Pro Lys
        705                 710                 715

GCA TTG AAC AGC AAA ATG TTT GCT GTC ATT GAA GGC GTG CGA GAA GAC     1897
Ala Leu Asn Ser Lys Met Phe Ala Val Ile Glu Gly Val Arg Glu Asp
    720                 725                 730

CTC CAA CCT CCA TCT CAA AGA GGA TCC TTC ATA CGA ACT CTC TCT GGA     1945
Leu Gln Pro Pro Ser Gln Arg Gly Ser Phe Ile Arg Thr Leu Ser Gly
735                 740                 745                 750

CAC AGA GTC TAT GGA TAT GCT CCA GAT GGG GTA CTT CCA CTG GAG ACT     1993
His Arg Val Tyr Gly Tyr Ala Pro Asp Gly Val Leu Pro Leu Glu Thr
                755                 760                 765

GGG AGA GAC TAC ACC GTT GTC CCA ATA GAT GAT GTC TGG GAC GAC AGC     2041
Gly Arg Asp Tyr Thr Val Val Pro Ile Asp Asp Val Trp Asp Asp Ser
            770                 775                 780

ATT ATG CTG TCC AAA GAT CCC ATA CCT CCT ATT GTG GGA AAC AGT GGA     2089
Ile Met Leu Ser Lys Asp Pro Ile Pro Pro Ile Val Gly Asn Ser Gly
        785                 790                 795

AAT CTA GCC ATA GCT TAC ATG GAT GTG TTT CGA CCC AAA GTC CCA ATC     2137
Asn Leu Ala Ile Ala Tyr Met Asp Val Phe Arg Pro Lys Val Pro Ile
    800                 805                 810

CAT GTG GCT ATG ACG GGA GCC CTC AAT GCT TGT GGC GAG ATT GAG AAA     2185
His Val Ala Met Thr Gly Ala Leu Asn Ala Cys Gly Glu Ile Glu Lys
815                 820                 825                 830

GTA AGC TTT AGA AGC ACC AAG CTC GCC ACT GCA CAC CGA CTT GGC CTT     2233
Val Ser Phe Arg Ser Thr Lys Leu Ala Thr Ala His Arg Leu Gly Leu
                835                 840                 845

AGG TTG GCT GGT CCC GGA GCA TTC GAT GTA AAC ACC GGG CCC AAC TGG     2281
Arg Leu Ala Gly Pro Gly Ala Phe Asp Val Asn Thr Gly Pro Asn Trp
            850                 855                 860

GCA ACG TTC ATC AAA CGT TTC CCT CAC AAT CCA CGC GAC TGG GAC AGG     2329
Ala Thr Phe Ile Lys Arg Phe Pro His Asn Pro Arg Asp Trp Asp Arg
        865                 870                 875

CTC CCC TAC CTC AAC CTA CCA TAC CTT CCA CCC AAT GCA GGA CGC CAG     2377
Leu Pro Tyr Leu Asn Leu Pro Tyr Leu Pro Pro Asn Ala Gly Arg Gln
    880                 885                 890

TAC CAC CTT GCC ATG GCT GCA TCA GAG TTC AAA GAG ACC CCC GAA CTC     2425
Tyr His Leu Ala Met Ala Ala Ser Glu Phe Lys Glu Thr Pro Glu Leu
895                 900                 905                 910

GAG AGT GCC GTC AGA GCA ATG GAA GCA GCA GCC AAC GTG GAC CCA CTA     2473
Glu Ser Ala Val Arg Ala Met Glu Ala Ala Ala Asn Val Asp Pro Leu
```

-continued

```
                915                 920                 925

TTC CAA TCT GCA CTC AGT GTG TTC ATG TGG CTG GAA GAG AAT GGG ATT      2521
Phe Gln Ser Ala Leu Ser Val Phe Met Trp Leu Glu Glu Asn Gly Ile
            930                 935                 940

GTG ACT GAC ATG GCC AAC TTC GCA CTC AGC GAC CCG AAC GCC CAT CGG      2569
Val Thr Asp Met Ala Asn Phe Ala Leu Ser Asp Pro Asn Ala His Arg
        945                 950                 955

ATG CGA AAT TTT CTT GCA AAC GCA CCA CAA GCA GGC AGC AAG TCG CAA      2617
Met Arg Asn Phe Leu Ala Asn Ala Pro Gln Ala Gly Ser Lys Ser Gln
    960                 965                 970

AGG GCC AAG TAC GGG ACA GCA GGC TAC GGA GTG GAG GCT CGG GGC CCC      2665
Arg Ala Lys Tyr Gly Thr Ala Gly Tyr Gly Val Glu Ala Arg Gly Pro
975                 980                 985                 990

ACA CCA GAG GAA GCA CAG AGG GAA AAA GAC ACA CGG ATC TCA AAG AAG      2713
Thr Pro Glu Glu Ala Gln Arg Glu Lys Asp Thr Arg Ile Ser Lys Lys
                995                1000                1005

ATG GAG ACC ATG GGC ATC TAC TTT GCA ACA CCA GAA TGG GTA GCA CTC      2761
Met Glu Thr Met Gly Ile Tyr Phe Ala Thr Pro Glu Trp Val Ala Leu
           1010                1015                1020

AAT GGG CAC CGA GGG CCA AGC CCC GGC CAG CTA AAG TAC TGG CAG AAC      2809
Asn Gly His Arg Gly Pro Ser Pro Gly Gln Leu Lys Tyr Trp Gln Asn
       1025                1030                1035

ACA CGA GAA ATA CCG GAC CCA AAC GAG GAC TAT CTA GAC TAC GTG CAT      2857
Thr Arg Glu Ile Pro Asp Pro Asn Glu Asp Tyr Leu Asp Tyr Val His
   1040                1045                1050

GCA GAG AAG AGC CGG TTG GCA TCA GAA GAA CAA ATC CTA AGG GCA GCT      2905
Ala Glu Lys Ser Arg Leu Ala Ser Glu Glu Gln Ile Leu Arg Ala Ala
1055                1060                1065                1070

ACG TCG ATC TAC GGG GCT CCA GGA CAG GCA GAG CCA CCC CAA GCT TTC      2953
Thr Ser Ile Tyr Gly Ala Pro Gly Gln Ala Glu Pro Pro Gln Ala Phe
               1075                1080                1085

ATA GAC GAA GTT GCC AAA GTC TAT GAA ATC AAC CAT GGA CGT GGC CCA      3001
Ile Asp Glu Val Ala Lys Val Tyr Glu Ile Asn His Gly Arg Gly Pro
           1090                1095                1100

AAC CAA GAA CAG ATG AAA GAT CTG CTC TTG ACT GCG ATG GAG ATG AAG      3049
Asn Gln Glu Gln Met Lys Asp Leu Leu Leu Thr Ala Met Glu Met Lys
       1105                1110                1115

CAT CGC AAT CCC AGG CGG GCT CTA CCA AAG CCC AAG CCA AAA CCC AAT      3097
His Arg Asn Pro Arg Arg Ala Leu Pro Lys Pro Lys Pro Lys Pro Asn
   1120                1125                1130

GCT CCA ACA CAG AGA CCC CCT GGT CGG CTG GGC CGC TGG ATC AGG ACC      3145
Ala Pro Thr Gln Arg Pro Pro Gly Arg Leu Gly Arg Trp Ile Arg Thr
1135                1140                1145                1150

GTC TCT GAT GAG GAC CTT GAG TGAGGCTCCT GGGAGTCTCC CGACACCACC         3196
Val Ser Asp Glu Asp Leu Glu
               1155

CGCGCAGGTG TGGACACCAA TTCGGCCTTA CAACATCCCA AATTGGATCC GTTCGCGGGT   3256

CCCCT                                                                3261
```

(2) INFORMATION FOR SEQ ID NO:30:

(i) SEQUENCE CHARACTERISTICS:
(A) LENGTH: 1012 amino acids
(B) TYPE: amino acid
(D) TOPOLOGY: linear (ii) MOLECULE TYPE: protein (xi) SEQUENCE DESCRIPTION: SEQ ID NO:30:

```
Met Thr Asn Leu Gln Asp Gln Thr Gln Gln Ile Val Pro Phe Ile Arg
```

-continued 1 5 10 15

Ser Leu Leu Met Pro Thr Thr Gly Pro Ala Ser Ile Pro Asp Asp Thr
20 25 30

Leu Glu Lys His Thr Leu Arg Ser Glu Thr Ser Thr Tyr Asn Leu Thr
35 40 45

Val Gly Asp Thr Gly Ser Gly Leu Ile Val Phe Phe Pro Gly Phe Pro
50 55 60

Gly Ser Ile Val Gly Ala His Tyr Thr Leu Gln Gly Asn Gly Asn Tyr
65 70 75 80

Lys Phe Asp Gln Met Leu Leu Thr Ala Gln Asn Leu Pro Ala Ser Tyr
85 90 95

Asn Tyr Cys Arg Leu Val Ser Arg Ser Leu Thr Val Arg Ser Ser Thr
100 105 110

Leu Pro Gly Gly Val Tyr Ala Leu Asn Gly Thr Ile Asn Ala Val Thr
115 120 125

Phe Gln Gly Ser Leu Ser Glu Leu Thr Asp Val Ser Tyr Asn Gly Leu
130 135 140

Met Ser Ala Thr Ala Asn Ile Asn Asp Lys Ile Gly Asn Val Leu Val
145 150 155 160

Gly Glu Gly Val Thr Val Leu Ser Leu Pro Thr Ser Tyr Asp Leu Gly
165 170 175

Tyr Val Arg Leu Gly Asp Pro Ile Pro Ala Ile Gly Leu Asp Pro Lys
180 185 190

Met Val Ala Thr Cys Asp Ser Ser Asp Arg Pro Arg Val Tyr Thr Ile
195 200 205

Thr Ala Ala Asp Asp Tyr Gln Phe Ser Ser Gln Tyr Gln Pro Gly Gly
210 215 220

Val Thr Ile Thr Leu Phe Ser Ala Asn Ile Asp Ala Ile Thr Ser Leu
225 230 235 240

Ser Val Gly Gly Glu Leu Val Phe Gln Thr Ser Val His Gly Leu Val
245 250 255

Leu Gly Ala Thr Ile Tyr Leu Ile Gly Phe Asp Gly Thr Thr Val Ile
260 265 270

Thr Arg Ala Val Ala Ala Asn Asn Gly Leu Thr Thr Gly Thr Asp Asn
275 280 285

Leu Met Pro Phe Asn Leu Val Ile Pro Thr Asn Glu Ile Thr Gln Pro
290 295 300

Ile Thr Ser Ile Lys Leu Glu Ile Val Thr Ser Lys Ser Gly Gly Gln
305 310 315 320

Ala Gly Asp Gln Met Ser Trp Ser Ala Arg Gly Ser Leu Ala Val Thr
325 330 335

Ile His Gly Gly Asn Tyr Pro Gly Ala Leu Arg Pro Val Thr Leu Val
340 345 350

Ala Tyr Glu Arg Val Ala Thr Gly Ser Val Val Thr Val Ala Gly Val
355 360 365

Ser Asn Phe Glu Leu Ile Pro Asn Pro Glu Leu Ala Lys Asn Leu Val
370 375 380

Thr Glu Tyr Gly Arg Phe Asp Pro Gly Ala Met Asn Tyr Thr Lys Leu
385 390 395 400

Ile Leu Ser Glu Arg Asp Arg Leu Gly Ile Lys Thr Val Trp Pro Thr
405 410 415

Arg Glu Tyr Thr Asp Phe Arg Glu Tyr Phe Met Glu Val Ala Asp Leu
420 425 430

-continued

```
Asn Ser Pro Leu Lys Ile Ala Gly Ala Phe Gly Phe Lys Asp Ile Ile
        435                 440                 445

Arg Ala Ile Arg Arg Ile Ala Val Pro Val Val Ser Thr Leu Phe Pro
    450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
            500                 505                 510

Ala Asp Lys Gly Tyr Glu Val Val Ala Asn Leu Phe Gln Val Pro Gln
        515                 520                 525

Asn Pro Val Val Asp Gly Ile Leu Ala Ser Pro Gly Val Leu Arg Gly
    530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
                565                 570                 575

Ser Lys Met Phe Ala Val Ile Glu Gly Val Arg Glu Asp Leu Gln Pro
            580                 585                 590

Pro Ser Gln Arg Gly Ser Phe Ile Arg Thr Leu Ser Gly His Arg Val
        595                 600                 605

Tyr Gly Tyr Ala Pro Asp Gly Val Leu Pro Leu Glu Thr Gly Arg Asp
    610                 615                 620

Tyr Thr Val Val Pro Ile Asp Asp Val Trp Asp Asp Ser Ile Met Leu
625                 630                 635                 640

Ser Lys Asp Pro Ile Pro Pro Ile Val Gly Asn Ser Gly Asn Leu Ala
                645                 650                 655

Ile Ala Tyr Met Asp Val Phe Arg Pro Lys Val Pro Ile His Val Ala
            660                 665                 670

Met Thr Gly Ala Leu Asn Ala Cys Gly Glu Ile Glu Lys Val Ser Phe
        675                 680                 685

Arg Ser Thr Lys Leu Ala Thr Ala His Arg Leu Gly Leu Arg Leu Ala
    690                 695                 700

Gly Pro Gly Ala Phe Asp Val Asn Thr Gly Pro Asn Trp Ala Thr Phe
705                 710                 715                 720

Ile Lys Arg Phe Pro His Asn Pro Arg Asp Trp Asp Arg Leu Pro Tyr
                725                 730                 735

Leu Asn Leu Pro Tyr Leu Pro Pro Asn Ala Gly Arg Gln Tyr His Leu
            740                 745                 750

Ala Met Ala Ala Ser Glu Phe Lys Glu Thr Pro Glu Leu Glu Ser Ala
        755                 760                 765

Val Arg Ala Met Glu Ala Ala Ala Asn Val Asp Pro Leu Phe Gln Ser
    770                 775                 780

Ala Leu Ser Val Phe Met Trp Leu Glu Glu Asn Gly Ile Val Thr Asp
785                 790                 795                 800

Met Ala Asn Phe Ala Leu Ser Asp Pro Asn Ala His Arg Met Arg Asn
                805                 810                 815

Phe Leu Ala Asn Ala Pro Gln Ala Gly Ser Lys Ser Gln Arg Ala Lys
            820                 825                 830

Tyr Gly Thr Ala Gly Tyr Gly Val Glu Ala Arg Gly Pro Thr Pro Glu
        835                 840                 845
```

-continued

```
Glu Ala Gln Arg Glu Lys Asp Thr Arg Ile Ser Lys Lys Met Glu Thr
    850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
                885                 890                 895

Ile Pro Asp Pro Asn Glu Asp Tyr Leu Asp Tyr Val His Ala Glu Lys
            900                 905                 910

Ser Arg Leu Ala Ser Glu Glu Gln Ile Leu Arg Ala Ala Thr Ser Ile
        915                 920                 925

Tyr Gly Ala Pro Gly Gln Ala Glu Pro Pro Gln Ala Phe Ile Asp Glu
    930                 935                 940

Val Ala Lys Val Tyr Glu Ile Asn His Gly Arg Gly Pro Asn Gln Glu
945                 950                 955                 960

Gln Met Lys Asp Leu Leu Leu Thr Ala Met Glu Met Lys His Arg Asn
                965                 970                 975

Pro Arg Arg Ala Leu Pro Lys Pro Lys Pro Lys Pro Asn Ala Pro Thr
            980                 985                 990

Gln Arg Pro Pro Gly Arg Leu Gly Arg Trp Ile Arg Thr Val Ser Asp
        995                 1000                1005

Glu Asp Leu Glu
    1010
```

(2) INFORMATION FOR SEQ ID NO:31:

(i) SEQUENCE CHARACTERISTICS:
(A) LENGTH: 3264 base pairs
(B) TYPE: nucleic acid
(C) STRANDEDNESS: single
(D) TOPOLOGY: circular (ii) MOLECULE TYPE: cDNA (ix) FEATURE:
(A) NAME/KEY: CDS
(B) LOCATION: 97..531

(xi) SEQUENCE DESCRIPTION: SEQ ID NO:31:

```
GGATACGATC GGTCTGACCC CGGGGGAGTC ACCCGGGGAC AGGCCATCAC TGCCTTGTTC      60

CTGGTTGGAA CTCCTCTTTC TGCTGTACTA TCGTTG ATG GTG AGT AGA GAT CAG       114
                                        Met Val Ser Arg Asp Gln
                                                1015

ACA AAC GAT CGC AGC GAT GAC AAA CCT GAT GGA TCA CAC CCA ACA GAT       162
Thr Asn Asp Arg Ser Asp Asp Lys Pro Asp Gly Ser His Pro Thr Asp
    1020                1025                1030

TGT TCC GTT CAT ACG GAG CCT TCT GAT GCC AAC GAC CGG ACC GGC GTC       210
Cys Ser Val His Thr Glu Pro Ser Asp Ala Asn Asp Arg Thr Gly Val
1035                1040                1045                1050

CAT TCC GGA CGA CAC CCT GGA GAA GCA CAC ACT CAG GTC CGA AAC CTC       258
His Ser Gly Arg His Pro Gly Glu Ala His Thr Gln Val Arg Asn Leu
                1055                1060                1065

GAC TTA CAA CTT GAC TGT AGG GGA TAC AGG GTC AGG ACT AAT TGT CTT       306
Asp Leu Gln Leu Asp Cys Arg Gly Tyr Arg Val Arg Thr Asn Cys Leu
            1070                1075                1080

TTT CCC TGG ATT CCC TGG TTC AGT TGT AGG TGC TCA CTA CAC ACT GCA       354
Phe Pro Trp Ile Pro Trp Phe Ser Cys Arg Cys Ser Leu His Thr Ala
        1085                1090                1095

GAG CAG TGG GAA CTA CCA ATT CGA CCA GAT GCT CCT GAC AGC GCA GAA       402
Glu Gln Trp Glu Leu Pro Ile Arg Pro Asp Ala Pro Asp Ser Ala Glu
    1100                1105                1110
```

-continued

```
CCT GCC TGC CAG CTA CAA CTA CTG CAG GCT AGT GAG CAG GAG TCT AAC      450
Pro Ala Cys Gln Leu Gln Leu Leu Gln Ala Ser Glu Gln Glu Ser Asn
1115                1120                1125                1130

CGT ACG GTC AAG CAC ACT CCC TGG TGG CGT TTA TGC ACT AAA CGG AAC      498
Arg Thr Val Lys His Thr Pro Trp Trp Arg Leu Cys Thr Lys Arg Asn
                1135                1140                1145

CAT AAA CGC AGT GAC CTT CCA CGG AAG CCT GAG TGAGTTGACT GACTACAGCT    551
His Lys Arg Ser Asp Leu Pro Arg Lys Pro Glu
            1150                1155

ACAACGGGCT GATGTCAGCC ACTGCGAACA TCAACGACAA GATCGGGAAC GTTCTAGTTG    611

GAGAAGGGGT GACTGTTCTC AGTCTACCGA CTTCATATGA CCTTAGTTAT GTGAGACTCG    671

GTGACCCCAT CCCCGCAGCA GGACTCGACC CGAAGTTGAT GGCCACGTGC GACAGTAGTG    731

ACAGACCCAG AGTCTACACC ATAACAGCTG CAGATGAATA CCAATTCTCG TCACAACTCA    791

TCCCGAGTGG CGTGAAGACC ACACTGTTCT CCGCCAACAT CGATGCTCTC ACCAGCTTCA    851

GCGTTGGTGG TGAGCTTGTC TTCAGCCAAG TAACGATCCA AAGCATTGAA GTGGACGTCA    911

CCATTCACTT CATTGGGTTT GACGGGACAG ACGTAGCAGT CAAGGCAGTT GCAACAGACT    971

TTGGGCTGAC AACTGGGACA AACAACCTTG TGCCATTCAA CCTGGTGGTC CCAACAAATG   1031

AGATCACCCA GCCCATCACT TCCATGAAAC TAGAGGTTGT GACCTACAAG ATTGGCGGCA   1091

CCGCTGGTGA CCCAATATCA TGGACAGTGA GTGGTACACT AGCTGTGACG GTGCACGGAG   1151

GCAACTACCC TGGGGCTCTC CGTCCTGTCA CCCTGGTGGC CTATGAACGA GTGGCTGCAG   1211

GATCTGTTGT CACAGTTGCA GGGGTGAGCA ACTTCGAGCT AATCCCCAAC CCTGAGCTTG   1271

CAAAGAACCT AGTTACAGAG TATGGCCGCT TTGACCCCGG AGCAATGAAC TACACCAAAC   1331

TAATACTGAG TGAGAGAGAT CGTCTAGGCA TCAAGACAGT CTGGCCCACC AGGGAGTACA   1391

CCGATTTCAG GGAGTACTTC ATGGAGGTTG CAGATCTCAA CTCACCCCTA AAGATTGCAG   1451

GAGCATTTGG CTTTAAGGAC ATAATCCGAG CCATTCGGAA GATTGCGGTG CCAGTGGTAT   1511

CCACACTCTT CCCTCCAGCT GCACCCCTAG CACATGCAAT CGGAGAAGGT GTAGACTACC   1571

TCCTGGGCGA CGAGGCCCAA GCAGCCTCAG GGACAGCTCG AGCCGCGTCA GGAAAAGCTA   1631

GAGCTGCCTC AGGACGAATA AGGCAGCTAA CTCTCGCAGC TGACAAGGGG TGCGAGGTAG   1691

TCGCCAACAT GTTCCAGGTG CCCCAGAATC CCATTGTTGA TGGCATTCTG GCATCCCCAG   1751

GAATCCTGCG TGGCGCACAC AACCTCGACT GCGTGCTATG GGAGGGAGCC ACTCTTTTCC   1811

CTGTTGTCAT TACGACACTC GAGGATGAGC TGACCCCCAA GGCACTGAAC AGCAAAATGT   1871

TTGCTGTCAT TGAAGGTGTG CGAGAGGACC TCCAGCCTCC ATCCCAACGG GGATCCTTCA   1931

TTCGAACTCT CTCTGGCCAT AGAGTCTATG GCTATGCCCC AGACGGAGTA CTGCCTCTGG   1991

AGACCGGGAG AGACTACACC GTTGTCCCAA TTGATGATGT GTGGGACGAT AGCATAATGC   2051

TGTCGCAGGA CCCCATACCT CCAATCATAG GGAACAGCGG CAACCTAGCC ATAGCATACA   2111

TGGATGTCTT CAGGCCCAAG GTCCCCATCC ACGTGGCTAT GACAGGGGCC CTCAATGCCC   2171

GCGGTGAGAT CGAGAGTGTT ACGTTCCGCA GCACCAAACT CGCCACAGCC CACCGACTTG   2231

GCATGAAGTT AGCTGGTCCT GGAGCCTATG ACATTAATAC AGGACCTAAC TGGGCAACGT   2291

TCGTCAAACG TTTCCCTCAC AATCCCCGAG ACTGGGACAG GTTGCCCTAC CTCAACCTTC   2351

CTTATCTCCC ACCAACAGCA GGACGTCAGT TCCATCTAGC CCTGGCTGCC TCCGAGTTCA   2411

AAGAGACCCC AGAACTCGAA GACGCTGTGC GCGCAATGGA TGCCGCTGCA AATGCCGACC   2471

CATTGTTCCG CTCAGCTCTC CAGGTCTTCA TGTGGTTGGA AGAAAACGGG ATTGTGACCG   2531
```

-continued

```
ACATGGCTAA CTTCGCCCTC AGCGACCCAA ACGCGCATAG GATGAAAAAC TTCCTAGCAA   2591

ACGCACCCCA GGCTGGAAGC AAGTCGCAGA GGGCCAAGTA TGGCACGGCA GGCTACGGAG   2651

TGGAGGCTCG AGGCCCCACA CCAGAAGAGG CACAGAGGGA AAAAGACACA CGGATCTCCA   2711

AGAAGATGGA AACAATGGGC ATCTACTTCG CGACACCGGA ATGGGTGGCT CTCAACGGGC   2771

ACCGAGGCCC AAGCCCCGGC CAACTCAAGT ACTGGCAAAA CACAAGAGAA ATACCAGAGC   2831

CCAATGAGGA CTACCCAGAC TATGTGCACG CGGAGAAGAG CCGGTTGGCG TCAGAAGAAC   2891

AGATCCTACG GGCAGCCACG TCGATCTACG GGGCTCCAGG ACAGGCTGAA CCACCCCAGG   2951

CCTTCATAGA CGAGGTCGCC AGGGTCTATG AAATCAACCA TGGGCGTGGT CCAAACCAGG   3011

AGCAGATGAA GGACCTGCTC CTGACTGCGA TGGAGATGAA GCATCGCAAT CCCAGGCGGG   3071

CTCCACCAAA GCCAAAGCCA AAACCCAATG CTCCATCACA GAGACCCCCT GGACGGCTGG   3131

GCCGCTGGAT CAGGACGGTC TCCGACGAGG ACTTGGAGTG AGGCTCCTGG GAGTCTCCCG   3191

ACACTACCCG CGCAGGTGTG GACACCAATT CGGCCTTCTA CCATCCCAAA TTGGATCCGT   3251

TCGCGGGTCC CCT                                                      3264
```

(2) INFORMATION FOR SEQ ID NO:32:

(i) SEQUENCE CHARACTERISTICS:
(A) LENGTH: 145 amino acids
(B) TYPE: amino acid
(D) TOPOLOGY: linear (ii) MOLECULE TYPE: protein (xi) SEQUENCE DESCRIPTION: SEQ ID NO:32:

```
Met Val Ser Arg Asp Gln Thr Asn Asp Arg Ser Asp Asp Lys Pro Asp
  1               5                  10                  15

Gly Ser His Pro Thr Asp Cys Ser Val His Thr Glu Pro Ser Asp Ala
             20                  25                  30

Asn Asp Arg Thr Gly Val His Ser Gly Arg His Pro Gly Glu Ala His
         35                  40                  45

Thr Gln Val Arg Asn Leu Asp Leu Gln Leu Asp Cys Arg Gly Tyr Arg
     50                  55                  60

Val Arg Thr Asn Cys Leu Phe Pro Trp Ile Pro Trp Phe Ser Cys Arg
 65                  70                  75                  80

Cys Ser Leu His Thr Ala Glu Gln Trp Glu Leu Pro Ile Arg Pro Asp
                 85                  90                  95

Ala Pro Asp Ser Ala Glu Pro Ala Cys Gln Leu Gln Leu Leu Gln Ala
            100                 105                 110

Ser Glu Gln Glu Ser Asn Arg Thr Val Lys His Thr Pro Trp Trp Arg
        115                 120                 125

Leu Cys Thr Lys Arg Asn His Lys Arg Ser Asp Leu Pro Arg Lys Pro
    130                 135                 140

Glu
145
```

(2) INFORMATION FOR SEQ ID NO:33:

(i) SEQUENCE CHARACTERISTICS:
(A) LENGTH: 3264 base pairs
(B) TYPE: nucleic acid
(C) STRANDEDNESS: single
(D) TOPOLOGY: circular (ii) MOLECULE TYPE: cDNA -continued

```
    (ix) FEATURE:
          (A) NAME/KEY: CDS
          (B) LOCATION: 131..3169

    (xi) SEQUENCE DESCRIPTION: SEQ ID NO:33:

GGATACGATC GGTCTGACCC CGGGGGAGTC ACCCGGGGAC AGGCCATCAC TGCCTTGTTC     60

CTGGTTGGAA CTCCTCTTTC TGCTGTACTA TCGTTGATGG TGAGTAGAGA TCAGACAAAC    120

GATCGCAGCG ATG ACA AAC CTG ATG GAT CAC ACC CAA CAG ATT GTT CCG       169
           Met Thr Asn Leu Met Asp His Thr Gln Gln Ile Val Pro
                           150                 155

TTC ATA CGG AGC CTT CTG ATG CCA ACG ACC GGA CCG GCG TCC ATT CCG      217
Phe Ile Arg Ser Leu Leu Met Pro Thr Thr Gly Pro Ala Ser Ile Pro
    160                 165                 170

GAC GAC ACC CTG GAG AAG CAC ACA CTC AGG TCC GAA ACC TCG ACT TAC      265
Asp Asp Thr Leu Glu Lys His Thr Leu Arg Ser Glu Thr Ser Thr Tyr
175                 180                 185                 190

AAC TTG ACT GTA GGG GAT ACA GGG TCA GGA CTA ATT GTC TTT TTC CCT      313
Asn Leu Thr Val Gly Asp Thr Gly Ser Gly Leu Ile Val Phe Phe Pro
                195                 200                 205

GGA TTC CCT GGT TCA GTT GTA GGT GCT CAC TAC ACA CTG CAG AGC AGT      361
Gly Phe Pro Gly Ser Val Val Gly Ala His Tyr Thr Leu Gln Ser Ser
            210                 215                 220

GGG AAC TAC CAA TTC GAC CAG ATG CTC CTG ACA GCG CAG AAC CTG CCT      409
Gly Asn Tyr Gln Phe Asp Gln Met Leu Leu Thr Ala Gln Asn Leu Pro
        225                 230                 235

GCC AGC TAC AAC TAC TGC AGG CTA GTG AGC AGG AGT CTA ACC GTA CGG      457
Ala Ser Tyr Asn Tyr Cys Arg Leu Val Ser Arg Ser Leu Thr Val Arg
    240                 245                 250

TCA AGC ACA CTC CCT GGT GGC GTT TAT GCA CTA AAC GGA ACC ATA AAC      505
Ser Ser Thr Leu Pro Gly Gly Val Tyr Ala Leu Asn Gly Thr Ile Asn
255                 260                 265                 270

GCA GTG ACC TTC CAC GGA AGC CTG AGT GAG TTG ACT GAC TAC AGC TAC      553
Ala Val Thr Phe His Gly Ser Leu Ser Glu Leu Thr Asp Tyr Ser Tyr
                275                 280                 285

AAC GGG CTG ATG TCA GCC ACT GCG AAC ATC AAC GAC AAG ATC GGG AAC      601
Asn Gly Leu Met Ser Ala Thr Ala Asn Ile Asn Asp Lys Ile Gly Asn
            290                 295                 300

GTT CTA GTT GGA GAA GGG GTG ACT GTT CTC AGT CTA CCG ACT TCA TAT      649
Val Leu Val Gly Glu Gly Val Thr Val Leu Ser Leu Pro Thr Ser Tyr
        305                 310                 315

GAC CTT AGT TAT GTG AGA CTC GGT GAC CCC ATC CCC GCA GCA GGA CTC      697
Asp Leu Ser Tyr Val Arg Leu Gly Asp Pro Ile Pro Ala Ala Gly Leu
    320                 325                 330

GAC CCG AAG TTG ATG GCC ACG TGC GAC AGT AGT GAC AGA CCC AGA GTC      745
Asp Pro Lys Leu Met Ala Thr Cys Asp Ser Ser Asp Arg Pro Arg Val
335                 340                 345                 350

TAC ACC ATA ACA GCT GCA GAT GAA TAC CAA TTC TCG TCA CAA CTC ATC      793
Tyr Thr Ile Thr Ala Ala Asp Glu Tyr Gln Phe Ser Ser Gln Leu Ile
                355                 360                 365

CCG AGT GGC GTG AAG ACC ACA CTG TTC TCC GCC AAC ATC GAT GCT CTC      841
Pro Ser Gly Val Lys Thr Thr Leu Phe Ser Ala Asn Ile Asp Ala Leu
            370                 375                 380

ACC AGC TTC AGC GTT GGT GGT GAG CTT GTC TTC AGC CAA GTA ACG ATC      889
Thr Ser Phe Ser Val Gly Gly Glu Leu Val Phe Ser Gln Val Thr Ile
        385                 390                 395

CAA AGC ATT GAA GTG GAC GTC ACC ATT CAC TTC ATT GGG TTT GAC GGG      937
Gln Ser Ile Glu Val Asp Val Thr Ile His Phe Ile Gly Phe Asp Gly
    400                 405                 410

ACA GAC GTA GCA GTC AAG GCA GTT GCA ACA GAC TTT GGG CTG ACA ACT      985
```

-continued

```
Thr Asp Val Ala Val Lys Ala Val Ala Thr Asp Phe Gly Leu Thr Thr
415                 420                 425                 430

GGG ACA AAC AAC CTT GTG CCA TTC AAC CTG GTG GTC CCA ACA AAT GAG     1033
Gly Thr Asn Asn Leu Val Pro Phe Asn Leu Val Val Pro Thr Asn Glu
                435                 440                 445

ATC ACC CAG CCC ATC ACT TCC ATG AAA CTA GAG GTT GTG ACC TAC AAG     1081
Ile Thr Gln Pro Ile Thr Ser Met Lys Leu Glu Val Val Thr Tyr Lys
            450                 455                 460

ATT GGC GGC ACC GCT GGT GAC CCA ATA TCA TGG ACA GTG AGT GGT ACA     1129
Ile Gly Gly Thr Ala Gly Asp Pro Ile Ser Trp Thr Val Ser Gly Thr
        465                 470                 475

CTA GCT GTG ACG GTG CAC GGA GGC AAC TAC CCT GGG GCT CTC CGT CCT     1177
Leu Ala Val Thr Val His Gly Gly Asn Tyr Pro Gly Ala Leu Arg Pro
    480                 485                 490

GTC ACC CTG GTG GCC TAT GAA CGA GTG GCT GCA GGA TCT GTT GTC ACA     1225
Val Thr Leu Val Ala Tyr Glu Arg Val Ala Ala Gly Ser Val Val Thr
495                 500                 505                 510

GTT GCA GGG GTG AGC AAC TTC GAG CTA ATC CCC AAC CCT GAG CTT GCA     1273
Val Ala Gly Val Ser Asn Phe Glu Leu Ile Pro Asn Pro Glu Leu Ala
                515                 520                 525

AAG AAC CTA GTT ACA GAG TAT GGC CGC TTT GAC CCC GGA GCA ATG AAC     1321
Lys Asn Leu Val Thr Glu Tyr Gly Arg Phe Asp Pro Gly Ala Met Asn
            530                 535                 540

TAC ACC AAA CTA ATA CTG AGT GAG AGA GAT CGT CTA GGC ATC AAG ACA     1369
Tyr Thr Lys Leu Ile Leu Ser Glu Arg Asp Arg Leu Gly Ile Lys Thr
        545                 550                 555

GTC TGG CCC ACC AGG GAG TAC ACC GAT TTC AGG GAG TAC TTC ATG GAG     1417
Val Trp Pro Thr Arg Glu Tyr Thr Asp Phe Arg Glu Tyr Phe Met Glu
    560                 565                 570

GTT GCA GAT CTC AAC TCA CCC CTA AAG ATT GCA GGA GCA TTT GGC TTT     1465
Val Ala Asp Leu Asn Ser Pro Leu Lys Ile Ala Gly Ala Phe Gly Phe
575                 580                 585                 590

AAG GAC ATA ATC CGA GCC ATT CGG AAG ATT GCG GTG CCA GTG GTA TCC     1513
Lys Asp Ile Ile Arg Ala Ile Arg Lys Ile Ala Val Pro Val Val Ser
                595                 600                 605

ACA CTC TTC CCT CCA GCT GCA CCC CTA GCA CAT GCA ATC GGA GAA GGT     1561
Thr Leu Phe Pro Pro Ala Ala Pro Leu Ala His Ala Ile Gly Glu Gly
            610                 615                 620

GTA GAC TAC CTC CTG GGC GAC GAG GCC CAA GCA GCC TCA GGG ACA GCT     1609
Val Asp Tyr Leu Leu Gly Asp Glu Ala Gln Ala Ala Ser Gly Thr Ala
        625                 630                 635

CGA GCC GCG TCA GGA AAA GCT AGA GCT GCC TCA GGA CGA ATA AGG CAG     1657
Arg Ala Ala Ser Gly Lys Ala Arg Ala Ala Ser Gly Arg Ile Arg Gln
    640                 645                 650

CTA ACT CTC GCA GCT GAC AAG GGG TGC GAG GTA GTC GCC AAC ATG TTC     1705
Leu Thr Leu Ala Ala Asp Lys Gly Cys Glu Val Val Ala Asn Met Phe
655                 660                 665                 670

CAG GTG CCC CAG AAT CCC ATT GTT GAT GGC ATT CTG GCA TCC CCA GGA     1753
Gln Val Pro Gln Asn Pro Ile Val Asp Gly Ile Leu Ala Ser Pro Gly
                675                 680                 685

ATC CTG CGT GGC GCA CAC AAC CTC GAC TGC GTG CTA TGG GAG GGA GCC     1801
Ile Leu Arg Gly Ala His Asn Leu Asp Cys Val Leu Trp Glu Gly Ala
            690                 695                 700

ACT CTT TTC CCT GTT GTC ATT ACG ACA CTC GAG GAT GAG CTG ACC CCC     1849
Thr Leu Phe Pro Val Val Ile Thr Thr Leu Glu Asp Glu Leu Thr Pro
        705                 710                 715

AAG GCA CTG AAC AGC AAA ATG TTT GCT GTC ATT GAA GGT GTG CGA GAG     1897
Lys Ala Leu Asn Ser Lys Met Phe Ala Val Ile Glu Gly Val Arg Glu
    720                 725                 730
```

-continued

```
GAC CTC CAG CCT CCA TCC CAA CGG GGA TCC TTC ATT CGA ACT CTC TCT      1945
Asp Leu Gln Pro Pro Ser Gln Arg Gly Ser Phe Ile Arg Thr Leu Ser
735                 740                 745                 750

GGC CAT AGA GTC TAT GGC TAT GCC CCA GAC GGA GTA CTG CCT CTG GAG      1993
Gly His Arg Val Tyr Gly Tyr Ala Pro Asp Gly Val Leu Pro Leu Glu
                755                 760                 765

ACC GGG AGA GAC TAC ACC GTT GTC CCA ATT GAT GAT GTG TGG GAC GAT      2041
Thr Gly Arg Asp Tyr Thr Val Val Pro Ile Asp Asp Val Trp Asp Asp
            770                 775                 780

AGC ATA ATG CTG TCG CAG GAC CCC ATA CCT CCA ATC ATA GGG AAC AGC      2089
Ser Ile Met Leu Ser Gln Asp Pro Ile Pro Pro Ile Ile Gly Asn Ser
        785                 790                 795

GGC AAC CTA GCC ATA GCA TAC ATG GAT GTC TTC AGG CCC AAG GTC CCC      2137
Gly Asn Leu Ala Ile Ala Tyr Met Asp Val Phe Arg Pro Lys Val Pro
    800                 805                 810

ATC CAC GTG GCT ATG ACA GGG GCC CTC AAT GCC CGC GGT GAG ATC GAG      2185
Ile His Val Ala Met Thr Gly Ala Leu Asn Ala Arg Gly Glu Ile Glu
815                 820                 825                 830

AGT GTT ACG TTC CGC AGC ACC AAA CTC GCC ACA GCC CAC CGA CTT GGC      2233
Ser Val Thr Phe Arg Ser Thr Lys Leu Ala Thr Ala His Arg Leu Gly
                835                 840                 845

ATG AAG TTA GCT GGT CCT GGA GCC TAT GAC ATT AAT ACA GGA CCT AAC      2281
Met Lys Leu Ala Gly Pro Gly Ala Tyr Asp Ile Asn Thr Gly Pro Asn
            850                 855                 860

TGG GCA ACG TTC GTC AAA CGT TTC CCT CAC AAT CCC CGA GAC TGG GAC      2329
Trp Ala Thr Phe Val Lys Arg Phe Pro His Asn Pro Arg Asp Trp Asp
        865                 870                 875

AGG TTG CCC TAC CTC AAC CTT CCT TAT CTC CCA CCA ACA GCA GGA CGT      2377
Arg Leu Pro Tyr Leu Asn Leu Pro Tyr Leu Pro Pro Thr Ala Gly Arg
    880                 885                 890

CAG TTC CAT CTA GCC CTG GCT GCC TCC GAG TTC AAA GAG ACC CCA GAA      2425
Gln Phe His Leu Ala Leu Ala Ala Ser Glu Phe Lys Glu Thr Pro Glu
895                 900                 905                 910

CTC GAA GAC GCT GTG CGC GCA ATG GAT GCC GCT GCA AAT GCC GAC CCA      2473
Leu Glu Asp Ala Val Arg Ala Met Asp Ala Ala Ala Asn Ala Asp Pro
                915                 920                 925

TTG TTC CGC TCA GCT CTC CAG GTC TTC ATG TGG TTG GAA GAA AAC GGG      2521
Leu Phe Arg Ser Ala Leu Gln Val Phe Met Trp Leu Glu Glu Asn Gly
            930                 935                 940

ATT GTG ACC GAC ATG GCT AAC TTC GCC CTC AGC GAC CCA AAC GCG CAT      2569
Ile Val Thr Asp Met Ala Asn Phe Ala Leu Ser Asp Pro Asn Ala His
        945                 950                 955

AGG ATG AAA AAC TTC CTA GCA AAC GCA CCC CAG GCT GGA AGC AAG TCG      2617
Arg Met Lys Asn Phe Leu Ala Asn Ala Pro Gln Ala Gly Ser Lys Ser
    960                 965                 970

CAG AGG GCC AAG TAT GGC ACG GCA GGC TAC GGA GTG GAG GCT CGA GGC      2665
Gln Arg Ala Lys Tyr Gly Thr Ala Gly Tyr Gly Val Glu Ala Arg Gly
975                 980                 985                 990

CCC ACA CCA GAA GAG GCA CAG AGG GAA AAA GAC ACA CGG ATC TCC AAG      2713
Pro Thr Pro Glu Glu Ala Gln Arg Glu Lys Asp Thr Arg Ile Ser Lys
                995                 1000                1005

AAG ATG GAA ACA ATG GGC ATC TAC TTC GCG ACA CCG GAA TGG GTG GCT      2761
Lys Met Glu Thr Met Gly Ile Tyr Phe Ala Thr Pro Glu Trp Val Ala
            1010                1015                1020

CTC AAC GGG CAC CGA GGC CCA AGC CCC GGC CAA CTC AAG TAC TGG CAA      2809
Leu Asn Gly His Arg Gly Pro Ser Pro Gly Gln Leu Lys Tyr Trp Gln
        1025                1030                1035

AAC ACA AGA GAA ATA CCA GAG CCC AAT GAG GAC TAC CCA GAC TAT GTG      2857
Asn Thr Arg Glu Ile Pro Glu Pro Asn Glu Asp Tyr Pro Asp Tyr Val
    1040                1045                1050
```

-continued

```
CAC GCG GAG AAG AGC CGG TTG GCG TCA GAA GAA CAG ATC CTA CGG GCA     2905
His Ala Glu Lys Ser Arg Leu Ala Ser Glu Glu Gln Ile Leu Arg Ala
1055                1060                1065                1070

GCC ACG TCG ATC TAC GGG GCT CCA GGA CAG GCT GAA CCA CCC CAG GCC     2953
Ala Thr Ser Ile Tyr Gly Ala Pro Gly Gln Ala Glu Pro Pro Gln Ala
                1075                1080                1085

TTC ATA GAC GAG GTC GCC AGG GTC TAT GAA ATC AAC CAT GGG CGT GGT     3001
Phe Ile Asp Glu Val Ala Arg Val Tyr Glu Ile Asn His Gly Arg Gly
            1090                1095                1100

CCA AAC CAG GAG CAG ATG AAG GAC CTG CTC CTG ACT GCG ATG GAG ATG     3049
Pro Asn Gln Glu Gln Met Lys Asp Leu Leu Leu Thr Ala Met Glu Met
        1105                1110                1115

AAG CAT CGC AAT CCC AGG CGG GCT CCA CCA AAG CCA AAG CCA AAA CCC     3097
Lys His Arg Asn Pro Arg Arg Ala Pro Pro Lys Pro Lys Pro Lys Pro
    1120                1125                1130

AAT GCT CCA TCA CAG AGA CCC CCT GGA CGG CTG GGC CGC TGG ATC AGG     3145
Asn Ala Pro Ser Gln Arg Pro Pro Gly Arg Leu Gly Arg Trp Ile Arg
1135                1140                1145                1150

ACG GTC TCC GAC GAG GAC TTG GAG TGAGGCTCCT GGGAGTCTCC CGACACTACC    3199
Thr Val Ser Asp Glu Asp Leu Glu
                1155

CGCGCAGGTG TGGACACCAA TTCGGCCTTC TACCATCCCA AATTGGATCC GTTCGCGGGT   3259

CCCCT                                                               3264
```

(2) INFORMATION FOR SEQ ID NO:34:

(i) SEQUENCE CHARACTERISTICS:
(A) LENGTH: 1013 amino acids
(B) TYPE: amino acid
(D) TOPOLOGY: linear (ii) MOLECULE TYPE: protein (xi) SEQUENCE DESCRIPTION: SEQ ID NO:34:

```
Met Thr Asn Leu Met Asp His Thr Gln Gln Ile Val Pro Phe Ile Arg
  1               5                  10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Val Val Gly Ala His Tyr Thr Leu Gln Ser Ser Gly Asn Tyr
 65                  70                  75                  80

Gln Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe His Gly Ser Leu Ser Glu Leu Thr Asp Tyr Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Ser
                165                 170                 175

Tyr Val Arg Leu Gly Asp Pro Ile Pro Ala Ala Gly Leu Asp Pro Lys
```

-continued

```
            180                 185                 190

Leu Met Ala Thr Cys Asp Ser Ser Asp Arg Pro Arg Val Tyr Thr Ile
        195                 200                 205

Thr Ala Ala Asp Glu Tyr Gln Phe Ser Ser Gln Leu Ile Pro Ser Gly
    210                 215                 220

Val Lys Thr Thr Leu Phe Ser Ala Asn Ile Asp Ala Leu Thr Ser Phe
225                 230                 235                 240

Ser Val Gly Gly Glu Leu Val Phe Ser Gln Val Thr Ile Gln Ser Ile
                245                 250                 255

Glu Val Asp Val Thr Ile His Phe Ile Gly Phe Asp Gly Thr Asp Val
            260                 265                 270

Ala Val Lys Ala Val Ala Thr Asp Phe Gly Leu Thr Thr Gly Thr Asn
        275                 280                 285

Asn Leu Val Pro Phe Asn Leu Val Val Pro Thr Asn Glu Ile Thr Gln
    290                 295                 300

Pro Ile Thr Ser Met Lys Leu Glu Val Val Thr Tyr Lys Ile Gly Gly
305                 310                 315                 320

Thr Ala Gly Asp Pro Ile Ser Trp Thr Val Ser Gly Thr Leu Ala Val
                325                 330                 335

Thr Val His Gly Gly Asn Tyr Pro Gly Ala Leu Arg Pro Val Thr Leu
            340                 345                 350

Val Ala Tyr Glu Arg Val Ala Ala Gly Ser Val Val Thr Val Ala Gly
        355                 360                 365

Val Ser Asn Phe Glu Leu Ile Pro Asn Pro Glu Leu Ala Lys Asn Leu
    370                 375                 380

Val Thr Glu Tyr Gly Arg Phe Asp Pro Gly Ala Met Asn Tyr Thr Lys
385                 390                 395                 400

Leu Ile Leu Ser Glu Arg Asp Arg Leu Gly Ile Lys Thr Val Trp Pro
                405                 410                 415

Thr Arg Glu Tyr Thr Asp Phe Arg Glu Tyr Phe Met Glu Val Ala Asp
            420                 425                 430

Leu Asn Ser Pro Leu Lys Ile Ala Gly Ala Phe Gly Phe Lys Asp Ile
        435                 440                 445

Ile Arg Ala Ile Arg Lys Ile Ala Val Pro Val Val Ser Thr Leu Phe
    450                 455                 460

Pro Pro Ala Ala Pro Leu Ala His Ala Ile Gly Glu Gly Val Asp Tyr
465                 470                 475                 480

Leu Leu Gly Asp Glu Ala Gln Ala Ala Ser Gly Thr Ala Arg Ala Ala
                485                 490                 495

Ser Gly Lys Ala Arg Ala Ala Ser Gly Arg Ile Arg Gln Leu Thr Leu
            500                 505                 510

Ala Ala Asp Lys Gly Cys Glu Val Val Ala Asn Met Phe Gln Val Pro
        515                 520                 525

Gln Asn Pro Ile Val Asp Gly Ile Leu Ala Ser Pro Gly Ile Leu Arg
    530                 535                 540

Gly Ala His Asn Leu Asp Cys Val Leu Trp Glu Gly Ala Thr Leu Phe
545                 550                 555                 560

Pro Val Val Ile Thr Thr Leu Glu Asp Glu Leu Thr Pro Lys Ala Leu
                565                 570                 575

Asn Ser Lys Met Phe Ala Val Ile Glu Gly Val Arg Glu Asp Leu Gln
            580                 585                 590

Pro Pro Ser Gln Arg Gly Ser Phe Ile Arg Thr Leu Ser Gly His Arg
        595                 600                 605
```

-continued

```
Val Tyr Gly Tyr Ala Pro Asp Gly Val Leu Pro Leu Glu Thr Gly Arg
    610                 615                 620

Asp Tyr Thr Val Val Pro Ile Asp Asp Val Trp Asp Asp Ser Ile Met
625                 630                 635                 640

Leu Ser Gln Asp Pro Ile Pro Pro Ile Ile Gly Asn Ser Gly Asn Leu
                645                 650                 655

Ala Ile Ala Tyr Met Asp Val Phe Arg Pro Lys Val Pro Ile His Val
            660                 665                 670

Ala Met Thr Gly Ala Leu Asn Ala Arg Gly Glu Ile Glu Ser Val Thr
        675                 680                 685

Phe Arg Ser Thr Lys Leu Ala Thr Ala His Arg Leu Gly Met Lys Leu
    690                 695                 700

Ala Gly Pro Gly Ala Tyr Asp Ile Asn Thr Gly Pro Asn Trp Ala Thr
705                 710                 715                 720

Phe Val Lys Arg Phe Pro His Asn Pro Arg Asp Trp Asp Arg Leu Pro
                725                 730                 735

Tyr Leu Asn Leu Pro Tyr Leu Pro Pro Thr Ala Gly Arg Gln Phe His
            740                 745                 750

Leu Ala Leu Ala Ala Ser Glu Phe Lys Glu Thr Pro Glu Leu Glu Asp
        755                 760                 765

Ala Val Arg Ala Met Asp Ala Ala Ala Asn Ala Asp Pro Leu Phe Arg
    770                 775                 780

Ser Ala Leu Gln Val Phe Met Trp Leu Glu Glu Asn Gly Ile Val Thr
785                 790                 795                 800

Asp Met Ala Asn Phe Ala Leu Ser Asp Pro Asn Ala His Arg Met Lys
                805                 810                 815

Asn Phe Leu Ala Asn Ala Pro Gln Ala Gly Ser Lys Ser Gln Arg Ala
            820                 825                 830

Lys Tyr Gly Thr Ala Gly Tyr Gly Val Glu Ala Arg Gly Pro Thr Pro
        835                 840                 845

Glu Glu Ala Gln Arg Glu Lys Asp Thr Arg Ile Ser Lys Lys Met Glu
    850                 855                 860

Thr Met Gly Ile Tyr Phe Ala Thr Pro Glu Trp Val Ala Leu Asn Gly
865                 870                 875                 880

His Arg Gly Pro Ser Pro Gly Gln Leu Lys Tyr Trp Gln Asn Thr Arg
                885                 890                 895

Glu Ile Pro Glu Pro Asn Glu Asp Tyr Pro Asp Tyr Val His Ala Glu
            900                 905                 910

Lys Ser Arg Leu Ala Ser Glu Glu Gln Ile Leu Arg Ala Ala Thr Ser
        915                 920                 925

Ile Tyr Gly Ala Pro Gly Gln Ala Glu Pro Pro Gln Ala Phe Ile Asp
    930                 935                 940

Glu Val Ala Arg Val Tyr Glu Ile Asn His Gly Arg Gly Pro Asn Gln
945                 950                 955                 960

Glu Gln Met Lys Asp Leu Leu Leu Thr Ala Met Glu Met Lys His Arg
                965                 970                 975

Asn Pro Arg Arg Ala Pro Pro Lys Pro Lys Pro Lys Pro Asn Ala Pro
            980                 985                 990

Ser Gln Arg Pro Pro Gly Arg Leu Gly Arg Trp Ile Arg Thr Val Ser
        995                 1000                1005

Asp Glu Asp Leu Glu
    1010
```